(12) United States Patent
Iwakiri et al.

(10) Patent No.: US 9,020,097 B2
(45) Date of Patent: Apr. 28, 2015

(54) RADIOGRAPHIC IMAGING SYSTEM

(75) Inventors: Naoto Iwakiri, Kanagawa (JP); Naoyuki Nishino, Kanagawa (JP); Haruyasu Nakatsugawa, Kanagawa (JP); Yutaka Yoshida, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 569 days.

(21) Appl. No.: 13/361,979

(22) Filed: Jan. 31, 2012

(65) Prior Publication Data

US 2012/0201351 A1     Aug. 9, 2012

(30) Foreign Application Priority Data

Feb. 8, 2011   (JP) ................. 2011-025292

(51) Int. Cl.
*G01T 1/24* (2006.01)
*A61B 6/00* (2006.01)
(Continued)

(52) U.S. Cl.
CPC ............ *A61B 6/4283* (2013.01); *A61B 6/4405* (2013.01); *A61B 6/4411* (2013.01); *A61B 6/4441* (2013.01); *A61B 6/4452* (2013.01); *A61B 6/487* (2013.01); *A61B 6/545* (2013.01); *A61B 6/56* (2013.01); *H04N 5/32* (2013.01); *H04N 5/353* (2013.01); *A61B 6/4423* (2013.01); *A61B 6/548* (2013.01)

(58) Field of Classification Search
CPC ...................................... A61B 6/487
USPC .................................... 378/42, 62
See application file for complete search history.

(56) References Cited

U.S. PATENT DOCUMENTS

2009/0001276 A1 *  1/2009  Yagi et al. ............... 250/370.09
2010/0046710 A1    2/2010  Ohishi

FOREIGN PATENT DOCUMENTS

JP         6-304162 A      11/1994
JP         2006-130158      5/2006
JP         2008-272454     11/2008
(Continued)

OTHER PUBLICATIONS

Partial English language translation of the following: Office action dated Feb. 4, 2014 from the Japanese Patent Office in a Japanese patent application corresponding to the instant patent application.
(Continued)

*Primary Examiner* — Glen Kao
*Assistant Examiner* — Danielle Fox
(74) *Attorney, Agent, or Firm* — Solaris Intellectual Property Group, PLLC

(57) ABSTRACT

There is provided a radiographic imaging system that has: a radiographic imaging device at which fluoroscopic imaging, that carries out capturing of radiographic images continuously, is possible; a radiation irradiating device that irradiates radiation in a pulse form with respect to the radiographic imaging device at a time of fluoroscopic imaging; and a controller that controls the radiation irradiating device such that radiation is pulse-irradiated at the radiographic imaging device with a proportion of an irradiation time period of radiation being set within a range of 12.5% to 80% with respect to each frame time period for capturing respective frame images according to a frame rate of fluoroscopic imaging, while capturing of radiographic images is carried out at the radiographic imaging device synchronously with the pulse irradiation.

13 Claims, 21 Drawing Sheets

(51) Int. Cl.
*H04N 5/32* (2006.01)
*H04N 5/353* (2011.01)

(56) References Cited

FOREIGN PATENT DOCUMENTS

| JP | 2009-017476 A | 1/2009 |
| JP | 2009-50531 | 3/2009 |
| JP | 2010-152279 | 7/2010 |

OTHER PUBLICATIONS

Partial English language translation of the following: Office action dated May 27, 2014 from the Japanese Patent Office in a Japanese patent application corresponding to the instant patent application.

\* cited by examiner

RADIOGRAPHIC IMAGING SYSTEM

CROSS-REFERENCE TO RELATED APPLICATION

This application is based on and claims priority under 35 USC 119 from Japanese Patent Application No. 2011-025292 filed on Feb. 8, 2011, which is incorporated by reference herein.

BACKGROUND

1. Technical Field

The present invention relates to a radiographic imaging system, and in particular, to a radiographic imaging system in which fluoroscopic imaging, that carries out capturing of radiographic images continuously, is possible.

2. Related Art

Radiation detectors such as FPDs (Flat Panel Detectors), in which a radiation-sensitive layer is disposed on a TFT (Thin Film Transistor) active matrix substrate and that can convert radiation directly into digital data, and the like have been put into practice in recent years. Portable radiographic imaging devices (hereinafter also called "electronic cassettes"), that capture radiographic images expressed by irradiated radiation by using the radiation detector, are being put into practice. As compared with a radiographic imaging device that uses a conventional X-ray film or imaging plate, a radiographic imaging device that uses the radiation detector has the advantages that images can be confirmed immediately, and fluoroscopic imaging (video imaging), in which the capturing of radiographic images is carried out continuously, also can be carried out. Note that, as methods of converting radiation at the radiation detector, there are an indirect conversion method that, after converting radiation into light at a scintillator, converts the light into charges at a semiconductor layer of photodiodes or the like, and a direct conversion method that converts radiation into charges at a semiconductor layer of amorphous selenium or the like, and the like. There exist various materials that can be used at the semiconductor layer in these respective methods.

As imaging methods for fluoroscopic imaging, there are a method of capturing images at a predetermined frame rate while irradiating radiation continuously from a radiation source (continuous irradiation), and a method of, while irradiating radiation in the form of pulses synchronously with the frame rate (pulse irradiation), capturing images synchronously with the irradiation of the radiation. With pulse irradiation, radiation can be irradiated for the time period needed for imaging, and the exposure dosage of the patient can be suppressed as compared with continuous irradiation, and there is therefore the advantage that the irradiated amount per unit time is increased. However, with pulse irradiation, there is the need to synchronize the timing of the image capturing at the radiation detector with the timing of irradiating the radiation from the radiation source.

Japanese Patent Application Laid-Open (JP-A) No. 2009-17476 discloses a technique of preventing deterioration in the S/N of a radiographic image and avoiding narrowing of the dynamic range, even in a case in which the frame rate is lowered as needed and the exposure dosage of the subject is reduced. In accordance with this technique, on the basis of the frame time of one frame, a first accumulation time, that relates to accumulation of charges that is carried out at the time of obtaining a radiographic image, is computed. If the first accumulation time is greater than a reference time that is a reference, a dummy accumulation time of charges is set within the frame time of one frame, and the first accumulation time is changed to a second accumulation time that is smaller than this first accumulation time. Then, image capturing processing of a radiographic image is carried out on the basis of the second accumulation time.

JP-A No. 6-304162 discloses a technique in which an incident X-ray amount detecting means is provided that detects an incident X-ray amount that has passed through a subject and is incident on a film, in a case in which pulse X-rays of a predetermined pulse interval that is in accordance with a predetermined tube voltage and tube current are generated from an X-ray tube and a tomogram of a cut section of the subject is captured on the film. The incident X-ray amount on the film, that is detected by the incident X-ray amount detecting means during the tomographic imaging, is integrated. When the integral value that is integrated per one pulse exceeds a threshold value of an incident X-ray amount that should be incident on the film, exposure of X-rays is cut-off.

In pulse irradiation, because the irradiation time period is short, the respective images may become frame-advanced images having stopped motion. This trend occurs in particular in cases in which the frame rate is low, because the imaging interval is large and after-images of the eyes also disappear.

SUMMARY

The present invention was made in order to overcome the above-described problematic points, and an object thereof is to provide a radiographic imaging system that can capture fluoroscopic images having smooth motion.

A radiographic imaging system according to a first aspect of the present invention includes: a radiographic imaging device at which fluoroscopic imaging, that carries out capturing of radiographic images continuously, is possible; a radiation irradiating device that irradiates radiation in a pulse form with respect to the radiographic imaging device at a time of fluoroscopic imaging; and a controller that controls the radiation irradiating device such that radiation is pulse-irradiated at the radiographic imaging device with a proportion of an irradiation time period of radiation being set within a range of 12.5% to 80% with respect to each frame time period for capturing respective frame images according to a frame rate of fluoroscopic imaging, while capturing of radiographic images is carried out at the radiographic imaging device synchronously with the pulse irradiation, A radiographic imaging system according to a second aspect of the present invention includes: a radiographic imaging device at which fluoroscopic imaging, that carries out capturing of radiographic images continuously, is possible; a radiation irradiating device that irradiates radiation in a pulse form with respect to the radiographic imaging device at a time of fluoroscopic imaging; and a non-transitory computer readable storage medium that stores a program that causes a computer to control the radiation irradiating device such that radiation is pulse-irradiated at the radiographic imaging device with a proportion of an irradiation time period of radiation being set within a range of 12.5% to 80% with respect to each frame time period for capturing respective frame images according to a frame rate of fluoroscopic imaging, while capturing of radiographic images is carried out at the radiographic imaging device synchronously with the pulse irradiation.

According to a third aspect of the present invention, a radiation controlling method for, a radiographic imaging system having a radiographic imaging device at which fluoroscopic imaging that carries out capturing of radiographic images continuously is possible, and the radiation irradiating device that irradiates radiation in a pulse form with respect to the radiographic imaging device at a time of fluoroscopic imaging, includes: controlling the radiation irradiating device such that radiation is pulse-irradiated at the radiographic imaging device with a proportion of an irradiation time period of radiation being set within a range of 12.5% to 80% with respect to each frame time period for capturing respective frame images according to a frame rate of fluoroscopic imaging, while capturing of radiographic images is carried out at the radiographic imaging device synchronously with the pulse irradiation.

BRIEF DESCRIPTION OF THE DRAWINGS

Exemplary embodiments of the present invention will be described in detail based on the following figures, wherein.

DETAILED DESCRIPTION

Exemplary embodiments of the present invention are described in detail hereinafter with reference to the drawings. Note that, here, description is given of an example of a case in which the present invention is applied to a radiology information system that is a system that all-inclusively manages information that is handled in the radiology department of a hospital.

Figure 1:
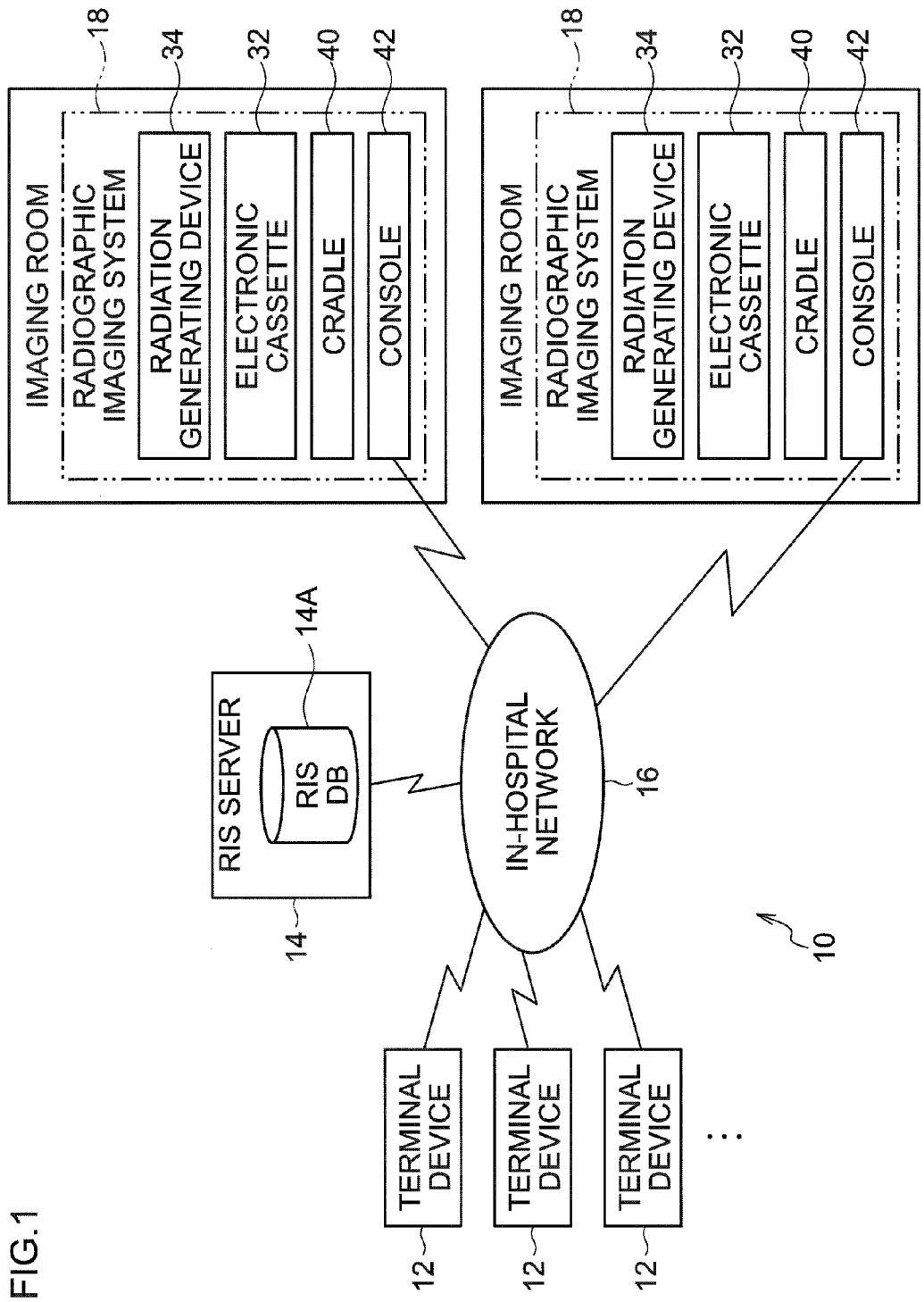
FIG. 1 is a block diagram showing the structure of a radiology information system relating to a first exemplary embodiment.

First, the structure of a radiology information system (hereinafter called "RIS") 10 relating to the present exemplary embodiment is described with reference to FIG. 1.

The RIS 10 is a system for carrying out information management such as scheduling of examinations/treatments, recording of diagnoses, and the like in a radiology department, and structures a part of a hospital information system (hereinafter called "HIS").

The RIS 10 has plural imaging requesting terminal devices (hereinafter called "terminal devices") 12, an RIS server 14, and radiographic imaging systems (hereinafter called "imaging systems") 18 that are individually set in radiographic imaging rooms (or operating rooms) within the hospital. The RIS 10 is structured such that these are respectively connected to an in-hospital network 16 that is formed from a wired or wireless LAN (Local Area Network) or the like. Note that the RIS 10 structures a part of the HIS that is provided within the same hospital. An HIS server (not illustrated) that manages the entire HIS also is connected to the in-hospital network 16.

The terminal device 12 is for a doctor or a radiologic technologist to carry out inputting, browsing, and the like of diagnostic data and reservations of facilities. Requests for capturing of radiographic images and reservations for imaging are also made via the terminal device 12. Each of the terminal devices 12 is structured to include a personal computer having a display device, and can communicate back and forth with the RIS server 14 via the in-hospital network 16.

On the other hand, the RIS server 14 accepts imaging requests from the respective terminal devices 12, and manages the imaging schedule of radiographic images at the imaging systems 18. The RIS server 14 is structured to include a database 14A.

The database 14A is structured to include data relating to patients such as attribute data (name, sex, birthdate, age, blood type, weight, patient ID, and the like) of a patient, the patient's history of past illness, history of past examinations/treatments, radiographic images that were captured in the past, and the like.

The imaging system 18 carries out capturing of radiographic images by the operation of a doctor or a radiologic technologist in accordance with instructions from the RIS server 14. The imaging system 18 has a radiation generating device 34, an electronic cassette 32 (radiographic imaging device), a cradle 40, and a console 42. The radiation generating device 34 irradiates, from a radiation source 130 (see FIG. 2 as well) and onto a subject, radiation X (see FIG. 3 as well) of a radiation amount according to exposure conditions. The electronic cassette 32 incorporates therein a radiation detector 60 (see FIG. 3 as well) that absorbs the radiation X that has been transmitted through the region to be imaged of the patient, and generates charges, and, on the basis of the generated charge amount, generates image data expressing a radiographic image. The cradle 40 charges a battery that is incorporated in the electronic cassette 32. The console 42 controls the electronic cassette 32, the radiation generating device 34, and the cradle 40.

Figure 2:
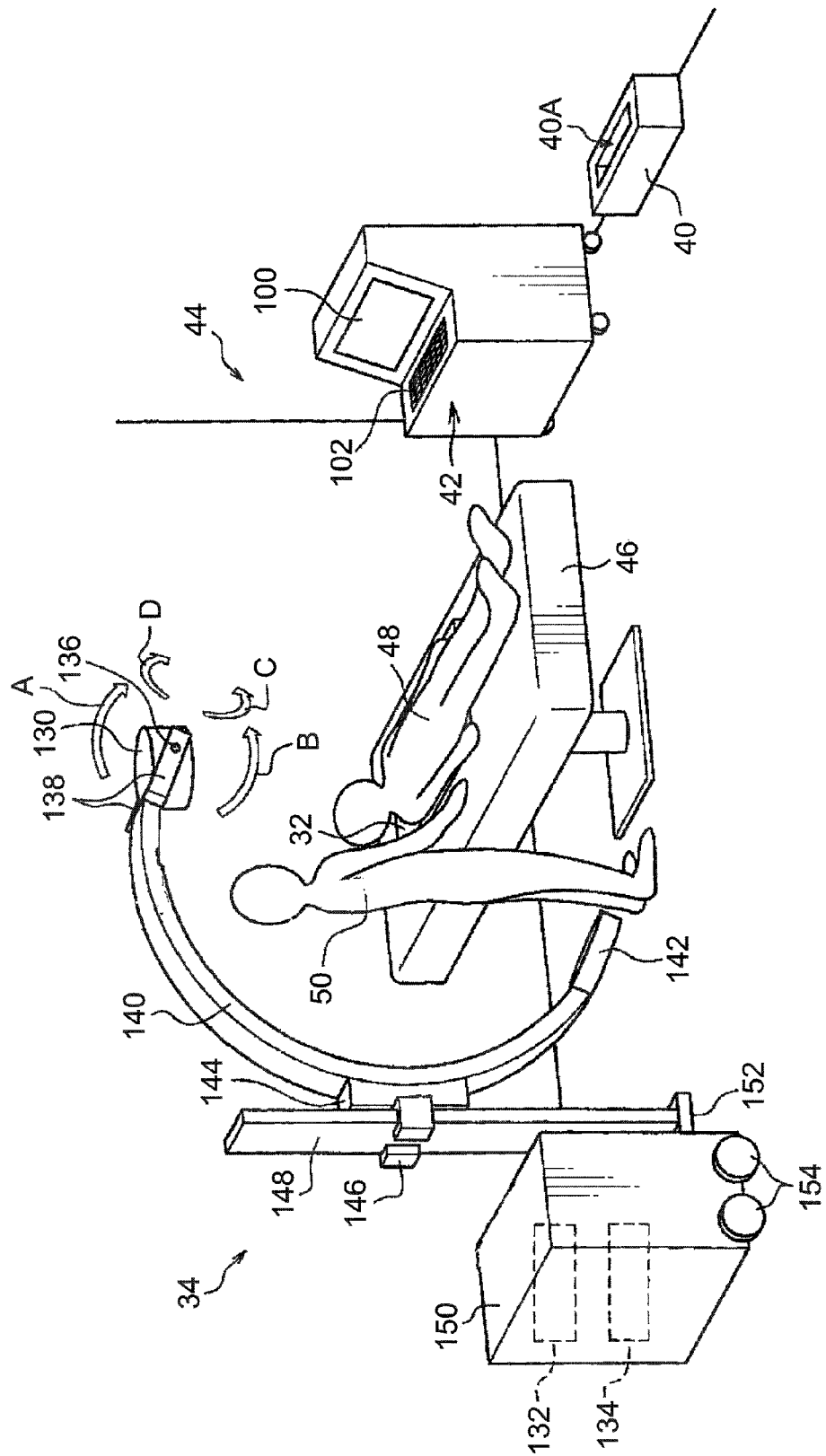
FIG. 2 is a perspective view showing an example of the state of placement of respective devices in a radiographic imaging room of a radiographic imaging system relating to the first exemplary embodiment, and the structure of a radiation generating device.

An example of the state of placement of respective devices, in a radiographic imaging room 44, of the imaging system 18 relating to the present exemplary embodiment, and the structure of the radiation generating device 34, are shown in FIG. 2. In the imaging system 18 relating to the present exemplary embodiment, the radiation generating device 34 and the console 42 are respectively connected by a cable, and carry out transmission and reception of various types of data by wired communication. However, the cable that connects the radiation generating device 34 and the console 42 is omitted from FIG. 2. Further, the transmission and reception of various types of data between the electronic cassette 32 and the console 42 may be carried out by wireless communication or wired communication.

The radiation generating device 34 relating to the present exemplary embodiment has a C arm 140. The radiation source 130 that emits the radiation X is provided at one end of the C arm 140. An attachment mechanism 142, to and from which the electronic cassette 32 can be attached and removed, is provided at the other end of the C arm 140. Note that FIG. 2 shows a state in which the electronic cassette 32 is removed from the attachment mechanism 142 and is provided between a bed 46, that is provided at the substantially central portion of the radiographic imaging room 44, and a subject (patient) 48 who is lying on the bed 46.

The radiation source 130 is provided at the one end of the C arm 140 via a supporting shaft 136 and a pair of supporting plates 138. The radiation source 130 can be rotated in direction A and direction B in FIG. 2 around the supporting shaft 136, and can be rotated together with the supporting plates 138 in direction C and direction D in FIG. 2 around a tangent line of the arc of the C arm 140.

A C arm holding portion 144, that holds the C arm 140 such that the C arm 140 can rotate clockwise and counterclockwise in FIG. 2, is provided at a position that abuts the outer periphery of the cylindrical surface of the C arm 140. On the other hand, the C arm holding portion 144 is held, via a C arm holding portion 146, at a support 148 so as to freely move vertically. Further, the C arm holding portion 144 is supported so as to be able to rotate around a horizontal axis with respect to the C arm holding portion 146.

On the other hand, the radiation generating device 34 has a main body portion 150 that incorporates therein a communication I/F unit 132, a radiation source controller 134, and the like that are described below. The lower end of the support 148 is mounted to a support supporting section 152 that projects-out to the side from a vicinity of the lower end portion of the housing of the main body portion 150.

Wheels 154 are provided at the bottom portion of the main body portion 150, such that the radiation generating device 34 can move within the hospital.

The cradle 40 and the console 42 are set in a vicinity of a wall surface in the radiographic imaging room 44 relating to the present exemplary embodiment.

An accommodating portion 40A that can accommodate the electronic cassette 32 is formed in the cradle 40.

During standby, the electronic cassette 32 is accommodated in the accommodating portion 40A of the cradle 40, and the battery incorporated within the electronic cassette 32 is charged. When capturing of a radiographic image is to be carried out, the electronic cassette 32 is removed from the cradle 40, and is either placed at a position corresponding to the region to be imaged of the subject 48 (the position shown in FIG. 2), or is mounted to the attachment mechanism 142 at the C arm 140 of the radiation generating device 34, and is utilized thereat.

Note that the electronic cassette 32 is not used only in radiographic imaging rooms and operating rooms. Because of the portability thereof, the electronic cassette 32 can be used also, for example, during medical examinations, and during rounds in a hospital, and the like.

Figure 3:
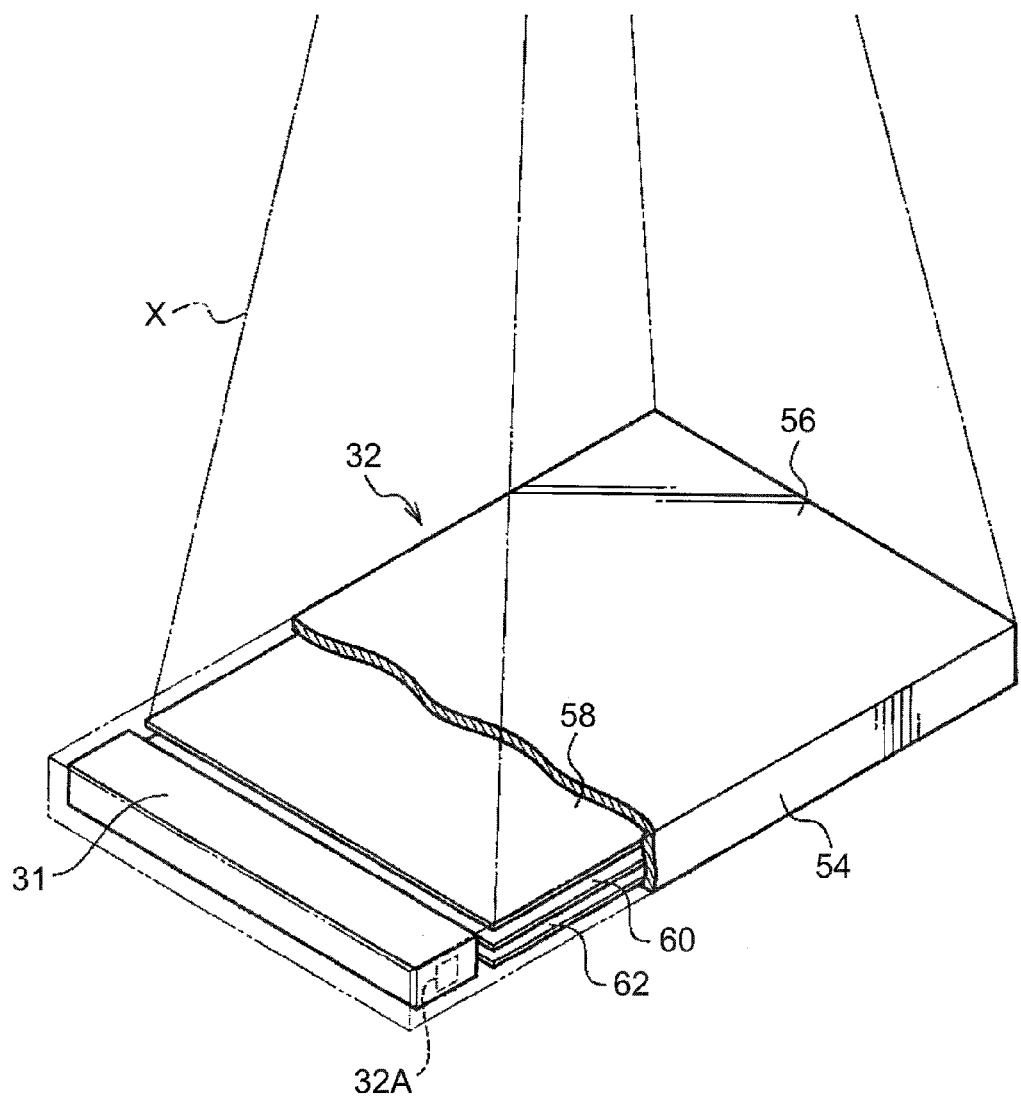
FIG. 3 is a transparent perspective view showing the internal structure of an electronic cassette relating to the first exemplary embodiment.

The internal structure of the electronic cassette 32 relating to the present exemplary embodiment is shown in FIG. 3.

As shown in FIG. 3, the electronic cassette 32 has a housing 54 formed from a material through which radiation X is transmitted, and is a structure that is waterproof and airtight. When the electronic cassette 32 is used in an operating room or the like, there is the concern that blood or other various germs will adhere thereto. Thus, the electronic cassette 32 is made to be a waterproof and airtight structure, and is disinfectingly cleaned as needed. Due thereto, the one electronic cassette 32 can be used repeatedly in continuation.

A grid 58, a radiation detector 60, and a lead plate 62 are disposed within the housing 54 in that order from an irradiated surface 56 side of the housing 54 on which the radiation X is irradiated. The grid 58 removes scattered radiation of the radiation X due to the patient. The radiation detector 60 detects the radiation X that has passed through the patient. The lead plate 62 absorbs the back-scattered radiation of the radiation X. Note that the irradiated surface 56 of the housing 54 may be structured as the grid 58. A connection terminal 32A for connecting a cable 43 is provided at a side surface of the housing 54.

A case 31, that accommodates electronic circuits including microcomputers and accommodates a secondary battery that is chargeable, is disposed at one end side of the interior of the housing 54. The radiation detector 60 and the electronic circuits are operated by electric power that is supplied from the secondary battery disposed in the case 31. In order to avoid damage, that accompanies irradiation of the radiation X, to the various types of circuits that are accommodated within the case 31, it is desirable to place a lead plate or the like at the irradiated surface 56 side of the case 31. Note that the electronic cassette 32 relating to the present exemplary embodiment is a parallelepiped at which the shape of the irradiated surface 56 is rectangular, and the case 31 is disposed at one end portion in the longitudinal direction thereof.

The main structures of the electrical system of the imaging system 18 relating to the present exemplary embodiment are described next with reference to FIG. 4.

A connection terminal 34A for carrying out communication with the console 42 is provided at the radiation generating device 34. A connection terminal 42A for carrying out communication with the radiation generating device 34 is provided at the console 42, and a connection terminal 42B for carrying out communication with the electronic cassette 32 is provided at the console 42. The connection terminal 34A of the radiation generating device 34 and the connection terminal 42A of the console 42 are connected by a cable 35.

In a case in which the electronic cassette 32 is to carry out wired communication, the cable 43 is connected to the connection terminal 32A, and the electronic cassette 32 is connected to the console 42 via the cable 43.

The radiation detector 60 incorporated within the electronic cassette 32 is structured by a photoelectric conversion layer, that absorbs the radiation X and converts the radiation X into charges, being layered on a TFT active matrix substrate 66. The photoelectric conversion layer is formed from, for example, amorphous a-Se (amorphous selenium) whose main component is selenium (e.g., a content of greater than or equal to 50%). When the radiation X is irradiated, the photoelectric conversion layer converts the irradiated radiation X into charges by generating, at the interior thereof, charges (pairs of electrons and holes) of a charge amount corresponding to the irradiated radiation amount. Note that, instead of a radiation-charge conversion material that directly converts the radiation X into charges such as amorphous selenium, the radiation detector 60 may convert the radiation X into charges indirectly by using a phosphor material and photoelectric conversion elements (photodiodes). Gadolinium oxysulfide ($Gd_2O_2S$:Tb) and cesium iodide (CsI:Tl) are well known as phosphor materials. In this case, conversion from the radiation X into light is carried out by the phosphor material, and conversion from light into charges is carried out by the photodiodes that are the photoelectric conversion elements.

Numerous pixel portions 74 having storage capacitors 68, that accumulate the charges generated at the photoelectric conversion layer, and TFTs 70, that are for reading-out the charges accumulated in the storage capacitors 68, are arranged in the form of a matrix on the TFT active matrix substrate 66. (In FIG. 4, the photoelectric conversion layer corresponding to the individual pixel portions 74 is shown schematically as sensor portions 72.) The charges, that are generated at the photoelectric conversion layer accompanying the irradiation of the radiation X onto the electronic cassette 32, are accumulated in the storage capacitors 68 of the individual pixel portions 74. Due thereto, the image data, that is carried by the radiation X irradiated on the electronic cassette 32, is converted into charge data and is held at the radiation detector 60.

Plural gate lines 76, that extend in a given direction (the row direction) and are for turning the TFTs 70 of the individual pixel portions 74 on and off, and plural data lines 78, that extend in a direction (the column direction) orthogonal to the gate lines 76 and are for reading-out the accumulated charges from the storage capacitors 68 via the TFTs 70 that have been turned on, are provided at the TFT active matrix substrate 66. The individual gate lines 76 are connected to a gate line driver 80, and the individual data lines 78 are connected to a signal processor 82. When charges are accumulated in the storage capacitors 68 of the individual pixel portions 74, the TFTs 70 of the individual pixel portions 74 are turned on in order in units of rows by signals supplied from the gate line driver 80 via the gate lines 76. The charges, that are accumulated in the storage capacitors 68 of the pixel portions 74 whose TFTs 70 have been turned on, are transferred through the data lines 78 as analog electrical signals and are inputted to the signal processor 82. Accordingly, the charges, that are accumulated in the storage capacitors 68 of the individual pixel portions 74, are read-out in order in units of rows.

Figure 5:
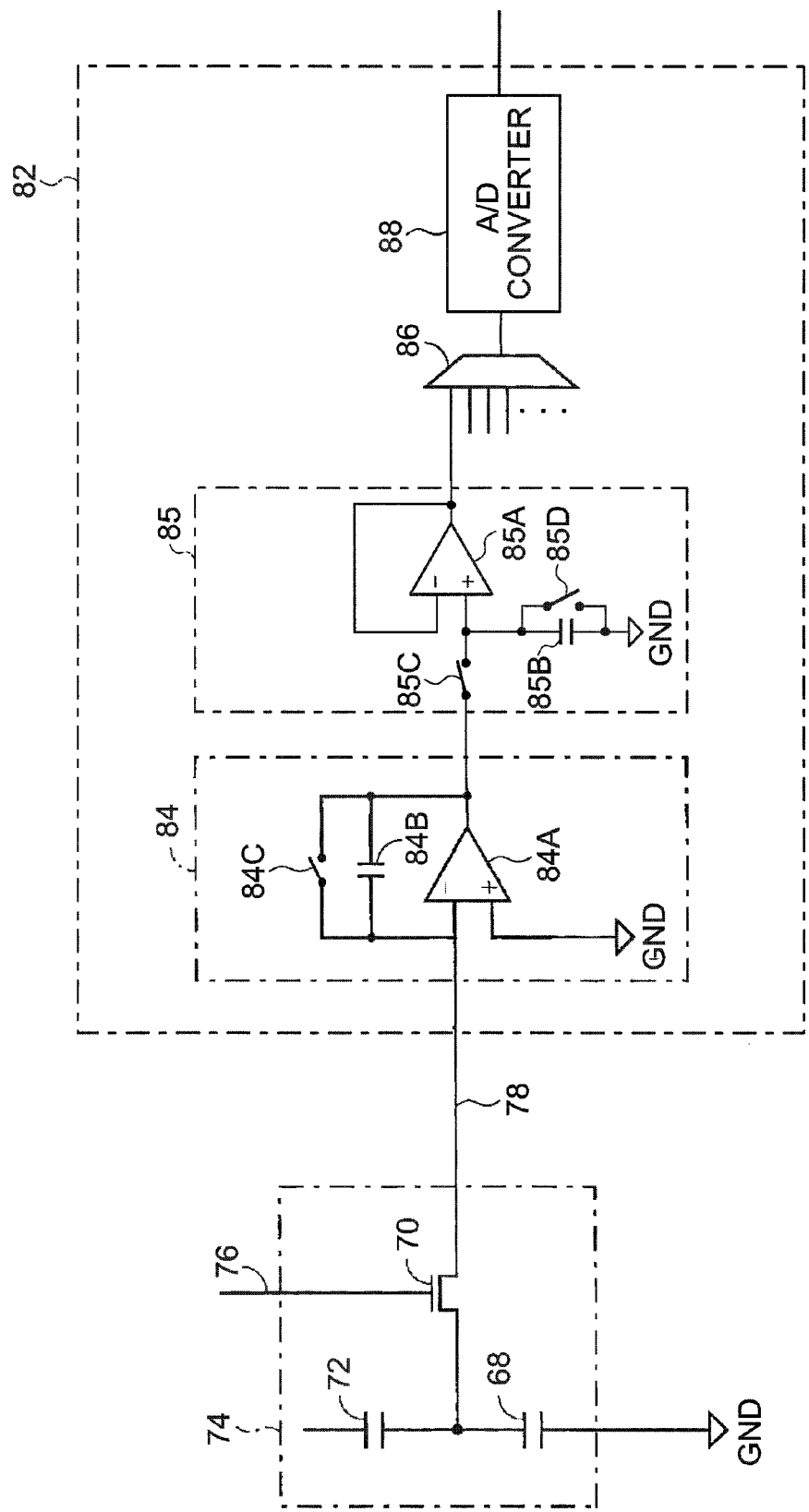
FIG. 5 is an equivalent circuit diagram that focuses on one pixel portion of a radiation detector relating to the first exemplary embodiment.

An equivalent circuit diagram, that focuses on one pixel portion of the radiation detector 60 relating to the present exemplary embodiment, is shown in FIG. 5.

As shown in FIG. 5, the source of the TFT 70 is connected to the data line 78, and the data line 78 is connected to the signal processor 82. The drain of the TFT 70 is connected to the storage capacitor 68 and the sensor portion 72, and the gate of the TFT 70 is connected to the gate line 76.

The signal processor 82 has a charge amplifier circuit 84 and a sample-and-hold circuit 85 for each of the individual data lines 78. The charge signals transmitted from the individual data lines 78 are converted into analog signals at the charge amplifying circuits 84, and are held in the sample-and-hold circuits 85.

The charge amplifier circuit 84 is structured to include an operational amplifier 84A and a capacitor 84B, and converts charge signals into analog voltages. Further, a switch 84C, that serves as a resetting circuit that shorts both electrodes of the capacitor 84B and releases the charges accumulated in the capacitor 84B, is provided at the charge amplifier circuit 84. The gain of the operational amplifier 84A can be adjusted in accordance with control from a cassette controller 92 that is described below.

The sample-and-hold circuit 85 is structured to include a buffer amplifier 85A and a capacitor 85B. In a state in which a switch 85C is shorted and is connected to the charge amplifier circuit 84, the sample-and-hold circuit 85 samples the voltage signal by using the capacitor 85B, and, when the switch 85C is opened, holds the voltage signal of the capacitor 85B at the point in time when the switch 85C opened. Further, the voltage signal that is held at the capacitor 85B can be reset by shorting a switch 85D that is provided as a resetting circuit that releases charges.

A multiplexer 86 and an A/D converter 88 are connected in that order to the output sides of the sample-and-hold circuits 85. The charge signals held in the individual sample-and-hold circuits are converted into analog voltages, are inputted in order (serially) to the multiplexer 86, and are converted into digital image data by the A/D converter 88.

Figure 4:
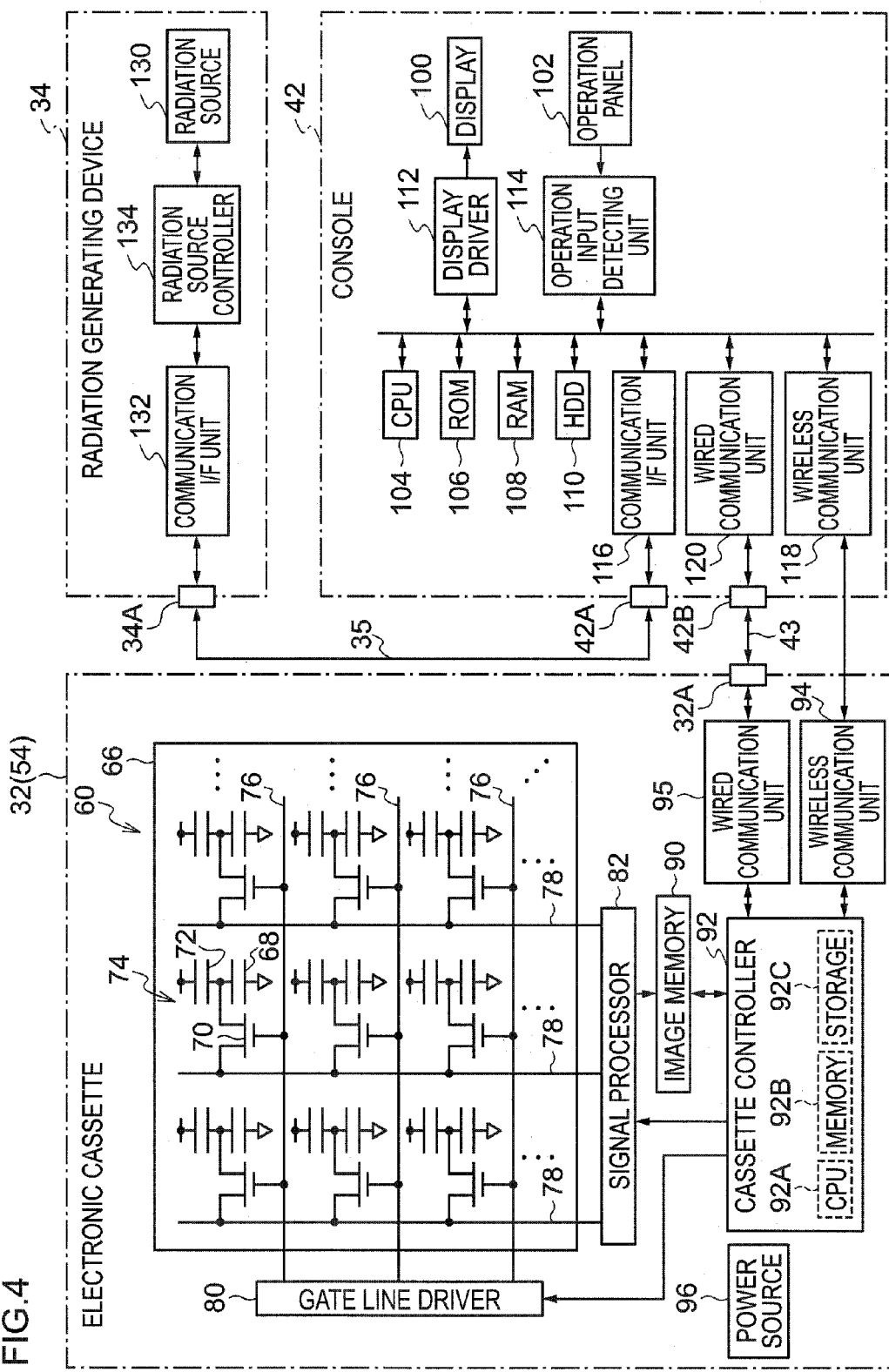
FIG. 4 is a block diagram showing the structures of main portions of the electrical system of the imaging system relating to the first exemplary embodiment.

An image memory 90 is connected to the signal processor 82 (see FIG. 4). The image data outputted from the A/D converter 88 of the signal processor 82 is stored in order in the image memory 90. The image memory 90 has a storage capacity that can store image data of plural frames. Each time capturing of a radiographic image is carried out, the image data obtained by the capturing are successively stored in the image memory 90.

The image memory 90 is connected to the cassette controller 92 that controls the overall operation of the electronic cassette 32. The cassette controller 92 is structured by a microcomputer, and has a CPU (Central Processing Unit) 92A, a memory 92B including a ROM (Read Only Memory) and a RAM (Random Access Memory), and a nonvolatile storage 92C formed by a HDD (Hard Disk Drive), a flash memory, or the like.

A wireless communication unit 94 and a wired communication unit 95 are connected to the cassette controller 92. The wireless communication unit 94 corresponds to wireless LAN (Local Area Network) standards such as IEEE (Institute of Electrical and Electronics Engineers) 802.11a/b/g/n or the like, and controls the transfer of various types of data to and from external devices by wireless communication. The wired communication unit 95 is connected to the connection terminal 32A, and controls the transfer of various types of data to and from the console 42 via the connection terminal 32A and the cable 43. The cassette controller 92 can communicate wirelessly with the console 42 via the wireless communication unit 94 or the wired communication unit 95, and carries out transmission and reception of various types of data to and from the console 42. The cassette controller 92 stores exposure conditions, that are described later and that are received from the console 42 via the wireless communication unit 94 or the wired communication unit 95, and starts the reading-out of charges on the basis of the exposure conditions.

Further, a power source 96 is provided at the electronic cassette 32. The above-described various types of circuits and respective elements (microcomputers and the like that function as the gate line driver 80, the signal processor 82, the image memory 90, the wireless communication unit 94, the wired communication unit 95 and the cassette controller 92), are operated by electric power supplied from the power source 96. The power source 96 incorporates therein the aforementioned battery (secondary battery) so that the portability of the electronic cassette 32 is not impaired, and supplies electric power from the charged battery to the various types of circuits and respective elements. Note that the wires, that connect the power source 96 with the various types of circuits and respective elements, are omitted from FIG. 4.

On the other hand, the console 42 is structured as a server computer, and has a display 100 that displays operation menus, captured radiographic images and the like, and an operation panel 102 that is structured to include plural keys and by which various types of data and operating instructions are inputted.

The console 42 relating to the present exemplary embodiment has a CPU 104 (controller, movement detecting unit), a ROM 106, a RAM 108, an HDD 110 (storage unit), a display driver 112, and an operation input detecting unit 114. The CPU 104 governs the operations of the overall device. Various types of programs including control programs, and the like, are stored in advance in the ROM 106. The RAM 108 temporarily stores various types of data. The HDD 110 stores and holds various types of data. The display driver 112 controls the display of various types of data on the display 100. The operation input detecting unit 114 detects the operated state of the operation panel 102. Further, the console 42 has a communication I/F unit 116, a wireless communication unit 118, and a wired communication unit 120. The communication I/F unit 116 is connected to the connection terminal 42A, and, via the connection terminal 42A and the cable 35, carries out transmission and reception of various types of data, such as exposure conditions that will be described later and the like, with the radiation generating device 34. The wireless communication unit 118 carries out transmission and reception of various types of data, such as exposure conditions and the like, with the electronic cassette 32 by wireless communication. The wired communication unit 120 is connected to the connection terminal 42B, and, via the connection terminal 42B and the cable 43, carries out transmission and reception of various types of data, such as image data and the like, with the electronic cassette 32.

The CPU 104, the ROM 106, the RAM 108, the HDD 110, the display driver 112, the operation input detecting unit 114, the wireless communication unit 118, and the wired communication unit 120 are connected to one another via a system bus BUS. Accordingly, the CPU 104 can access the ROM 106, the RAM 108 and the HDD 110, and can carry out control of display of various types of data on the display 100 via the display driver 112, control of the transmission and reception of various types of data to and from the radiation generating device 34 via the communication I/F unit 116, control of the transmission and reception of various types of data to and from the electronic cassette 32 via the wireless communication unit 118, and control of the transmission and reception of various types of data to and from the electronic cassette 32 via the wired communication unit 120. Further, the CPU 104 can learn of the operated state of the operation panel 102 by the user via the operation input detecting unit 114.

On the other hand, the radiation generating device 34 has the radiation source 130 that emits the radiation X, the communication I/F unit 132 that transmits and receives various types of data, such as exposure conditions and the like, to and from the console 42, and the radiation source controller 134 that controls the radiation source 130 on the basis of received exposure conditions.

The radiation source controller 134 as well is realized by a microcomputer, and stores the received exposure conditions, and causes the radiation X to be irradiated from the radiation source 130 on the basis of these exposure conditions.

Operation of the imaging system 18 relating to the present exemplary embodiment is described next.

Fluoroscopic imaging, in which imaging is carried out continuously, is possible at the electronic cassette 32 relating to the present exemplary embodiment. Further, if the electronic cassette 32 relating to the present exemplary embodiment and the console 42 are connected by the cable 43, wired communication is carried out therebetween. If the electronic cassette 32 and the console 42 are not connected by the cable 43, wireless communication is carried out therebetween.

For example, when carrying out fluoroscopic imaging of an affected part of the subject 48 who is lying on the bed 46 as shown in FIG. 2, if the communication between the electronic cassette 32 and the console 42 is to be made to be wireless communication, an operator 50 does not connect the cable 43 to the electronic cassette 32 and the console 42. If the communication between the electronic cassette 32 and the console 42 is to be made to be wired communication, the operator 50 connects the electronic cassette 32 and the console 42 by the cable 43, and thereafter, places the electronic cassette 32 between the bed 46 and the affected part of the subject 48 in accordance with the region that is to be imaged.

Then, at the operation panel 102, the operator 50 designates the exposure conditions such as the frame rate, the tube voltage, the tube current and the like.

Figure 6A:
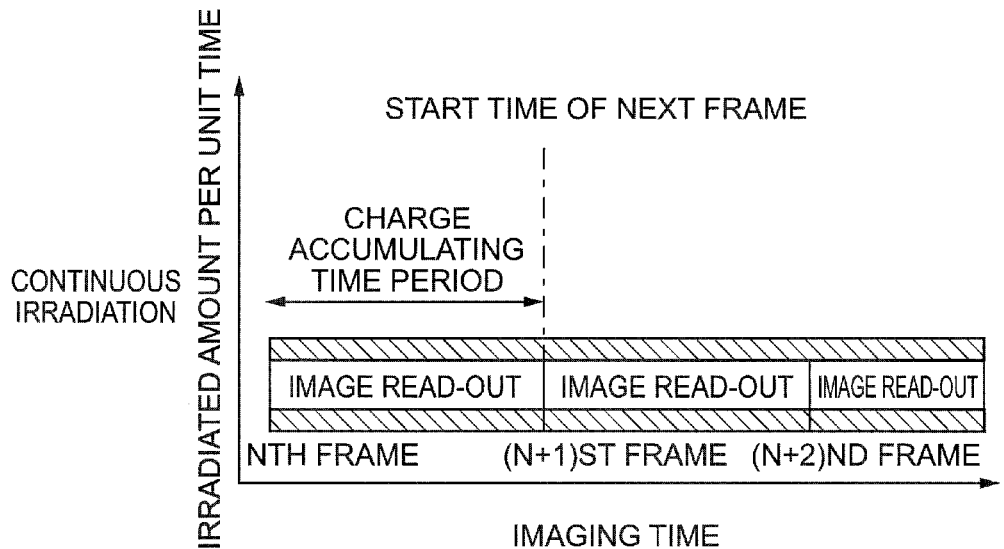
FIG. 6A is a time chart showing irradiation time periods of radiation by continuous irradiation, irradiated amounts of radiation per unit time, and image read-out timings, relating to the first exemplary embodiment.

As shown in FIG. 6A, in fluoroscopic imaging by continuous irradiation, radiation is irradiated continuously from the radiation source 130 during image capturing, and radiation is irradiated also at the time of image read-out. Therefore, there is the need to keep the irradiated amount of radiation per unit time low and suppress the exposure dosage of the subject 48.

Figure 6B:
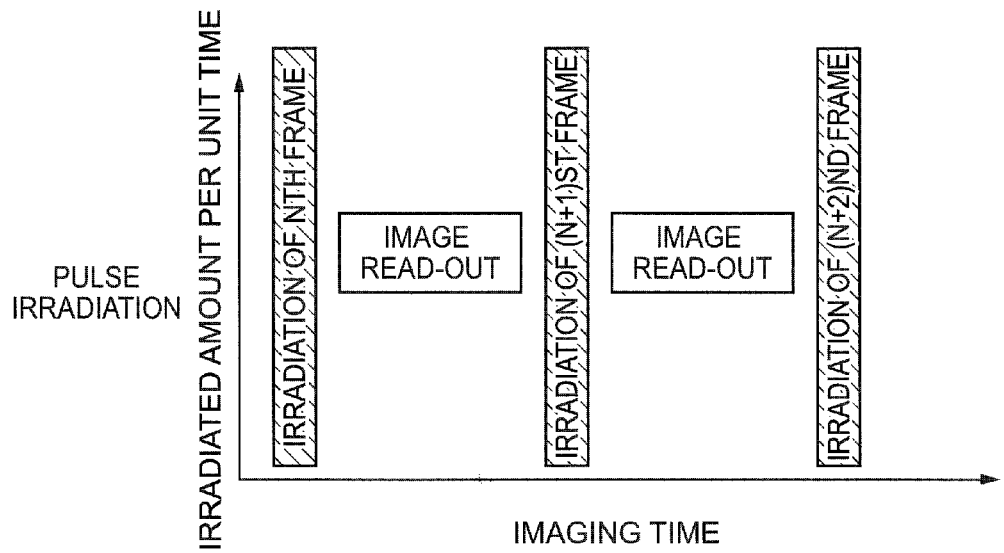
FIG. 6B is a time chart showing irradiation time periods of radiation by pulse irradiation, irradiated amounts of radiation per unit time, and image read-out timings, relating to the first exemplary embodiment.

On the other hand, as shown in FIG. 6B, in fluoroscopic imaging by pulse irradiation, radiation can be irradiated for only the time period needed for the image capturing, and the exposure dosage of the patient can be suppressed as compared with continuous irradiation. Therefore, there is the advantage that the irradiated amount per unit time can be increased.

Therefore, at the imaging system 18 relating to the present exemplary embodiment, fluoroscopic imaging is carried out by pulse irradiation.

In pulse irradiation, because the irradiation time period is short, the respective images may become frame-advanced images having stopped motion. In particular, in cases in which the frame rate is low, the imaging interval is large and after-images of the eyes also disappear, and therefore, fluoroscopic images having smooth motion cannot be captured.

Thus, in the present exemplary embodiment, in a case in which the frame rate of fluoroscopic imaging is low, the irradiated amount of radiation per unit time in the pulse irradiation of a single time is kept low, and the irradiation time period is made to be long within the respective frame time periods for capturing the respective frame images.

Here, the time resolution of a human eye is around 50 ms to 100 ms, and flashing of light that is shorter than this time is perceived as continuous lighting.

For example, following Table 1 shows results of evaluation when the frame rate is 5 fps and the proportion of the time period of pulse irradiation within one frame time period (within ⅕ of a second) is varied.

TABLE 1

| proportion X of irradiation time period within frame time period | 12.5% or less | 12.5% to 17% | 17% to 33% | 33% to 80% |
|---|---|---|---|---|
| evaluation | X there is a sense of frame dropping | Δ there is a sense of frame dropping, but it is an acceptable level | ◯ some frame dropping | ◎ no sense of frame dropping |

On the other hand, the frame time period must also include a read-out time period in which the accumulated charges are read-out. This read-out time period must be around 20% of the frame time period. Therefore, the upper limit of the time period in which radiation can be irradiated within the frame time period in pulse irradiation is around 80%.

Accordingly, in fluoroscopic imaging by pulse irradiation, in order to keep the sense of frame dropping to an acceptable level, the proportion of the irradiation time period with respect to the frame time period must be kept within a range of 12.5% to 80%, and within a range of 33% to 80% is more preferable.

In the present exemplary embodiment, the proportion of the irradiation time period of radiation with respect to each frame time period that corresponds to the frame rate of the fluoroscopic imaging is changed to 80%, and the exposure conditions such as the tube voltage, the tube current and the like are changed, and the irradiated amount of radiation per unit time also is changed. Note that, if the exposure conditions are changed and the irradiated amount of radiation per unit time is made to be too low, there are cases in which the minimum irradiated amount needed for capturing a radiographic image cannot be ensured. Thus, by dividing the minimum irradiated amount by the changed irradiation time period, the minimum irradiated amount of radiation per unit time that is needed for capturing a radiographic image is determined, and the exposure conditions, such as the tube voltage, the tube current and the like, are changed within a range in which this irradiated amount of radiation per unit time is obtained.

In the present exemplary embodiment, fluoroscopic imaging is carried out by, while pulse-irradiating radiation at the changed irradiation time period, repeatedly carrying out capturing of a radiographic image synchronously with this pulse irradiation.

At the console 42, when an operation that designates the exposure conditions such as the frame rate, the tube voltage, the tube current and the like is carried out at the operation panel 102, the irradiation time period is set by the irradiation time period setting processing that is described hereinafter.

Figure 7:
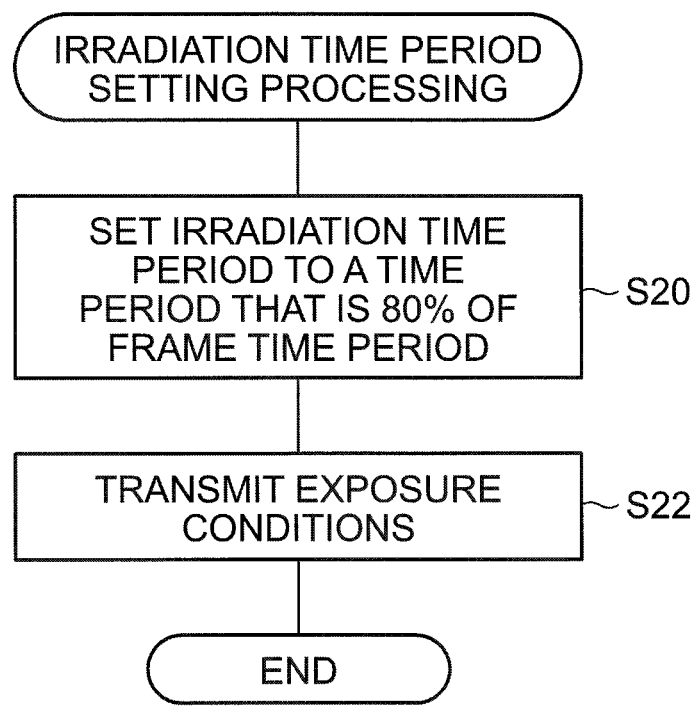
FIG. 7 is a flowchart showing the flow of processings of an irradiation time period setting processing program relating to the first exemplary embodiment.

A flowchart showing the flow of processings of an irradiation time period setting processing program, that is executed by the CPU 104 relating to the present exemplary embodiment, is shown in FIG. 7. Note that this program is stored in advance in a predetermined area of the HDD 110, and is executed at the time when a designating operation, that designates the imaging mode and the exposure conditions, is carried out at the operation panel 102.

In step S20 of FIG. 7, the CPU 104 sets the irradiation time period of the radiation in each pulse irradiation to be a time period that is 80% of the frame time period corresponding to the designated frame rate. Accompanying the changing of the irradiation time period, the CPU 104 also changes the exposure conditions such as the tube voltage, the tube current and the like, so as to lower the irradiated amount of radiation per unit time.

In step S22, the CPU 104 transmits the set irradiation time period, and the designated frame rate, tube voltage, tube current, and the like to the electronic cassette 32 and the radiation generating device 34 as exposure conditions, and ends the present irradiation time period setting processing program.

When preparations for image capturing are completed, the operator 50 carries out, at the operation panel 102 of the console 42, an imaging instructing operation that instructs image capturing.

When an imaging starting operation is carried out at the operation panel 102, the console 42 starts image capturing operations.

Figure 8:
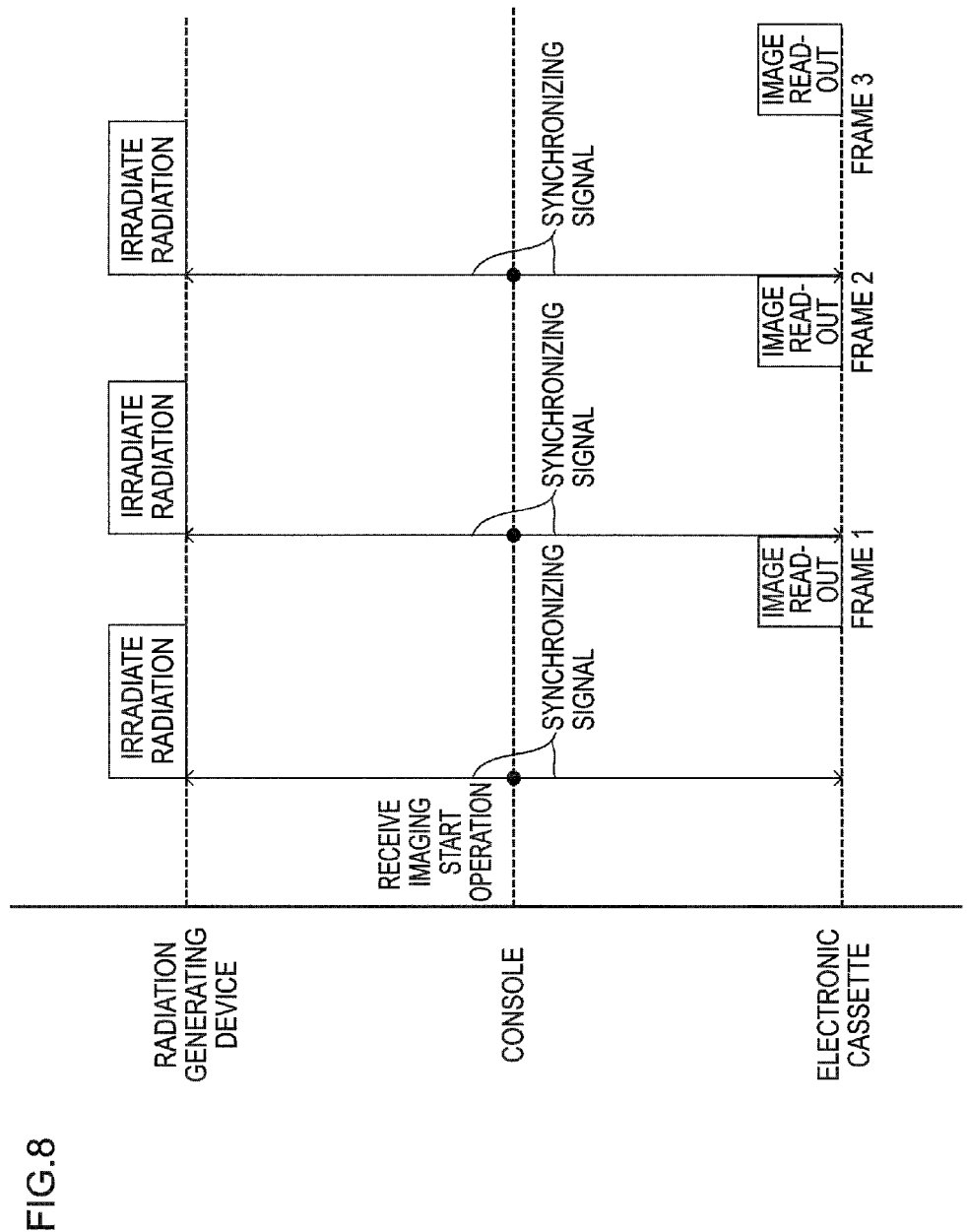
FIG. 8 is a time chart showing the flow of image capturing operations of fluoroscopic imaging relating to the first exemplary embodiment.

FIG. 8 is a time chart showing the flow of the image capturing operations at the time of carrying out fluoroscopic imaging by pulse irradiation.

The console 42 transmits, to the radiation generating device 34 and the electronic cassette 32, a synchronizing signal at a period corresponding to the designated frame rate.

Each time the radiation generating device 34 receives the synchronizing signal, the radiation generating device 34 generates and emits radiation at the tube voltage and tube current and for the irradiation time period that correspond to the exposure conditions received from the console 42.

After the irradiation time period that is designated in the exposure conditions elapses from the receipt of the synchronizing signal, the cassette controller 92 of the electronic cassette 32 controls the gate line driver 80 and causes on signals to be outputted from the gate line driver 80 to the respective gate lines 76 in order and line-by-line, and turns the respective TFTs 70, that are connected to the respective gate lines 76, on in order and line-by-line, and reads-out the image. The electrical signals that have flowed-out to the respective data lines 78 of the radiation detector 60 are converted into digital image data at the signal processor 82, are stored in the image memory 90, and are transmitted to the console 42 one image at a time. The images that are transmitted to the console 42 are subjected, at the console 42, to image processings that perform various types of corrections, such as shading correction and the like, and are stored in the HDD 110. The image data stored in the HDD 110 is displayed on the display 100 for confirmation of the captured radiographic images and the like, and is transferred to the RIS server 14 and stored in the database 14A as well.

Further, when an imaging end operation is carried out at the operation panel 102, the console 42 transmits instruction data that instructs the end of exposure to the radiation generating device 34 and the electronic cassette 32. Due thereto, the radiation source 130 stops irradiation of the radiation, and the electronic cassette 32 ends the reading-out of images.

Figure 9A:
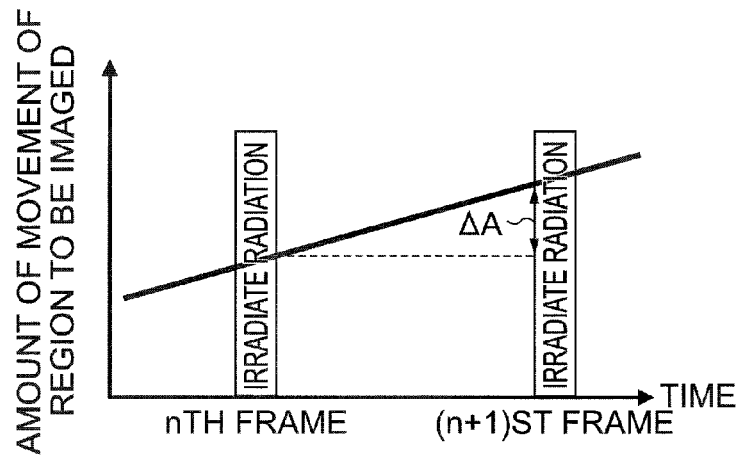
FIG. 9A is a graph showing an example of the relationship between an irradiation time period of radiation of conventional fluoroscopic imaging, and an amount of movement at a time when a region to be imaged moves.

Here, for example, in conventional fluoroscopic imaging, fluoroscopic imaging is carried out by carrying out pulse irradiation with the irradiation time period of the radiation being a relatively short time period as shown in FIG. 9A. Therefore, for example, if the region to be imaged moves as shown by the straight line, the region to be imaged moves by AA during the time from the irradiation of the nth frame to the start of irradiation of the n+1st frame, and the change in the region to be imaged during this time is omitted from the radiographic image.

Figure 9B:
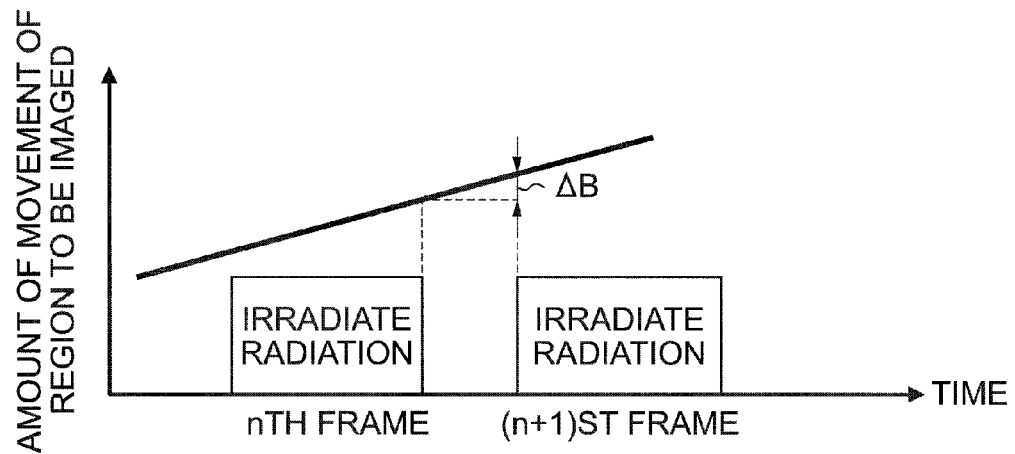
FIG. 9B is a graph showing an example of the relationship between an irradiation time period of radiation of fluoroscopic imaging relating to the first exemplary embodiment, and an amount of movement at a time when a region to be imaged moves.

On the other hand, in a case of carrying out fluoroscopic imaging by changing the irradiation time period of the radiation as in the present exemplary embodiment, as shown in FIG. 9B, if the region to be imaged moves as shown by the straight line, the region to be imaged moves by ΔB during the time from the irradiation of the nth frame to the start of irradiation of the n+1st frame. However, by making the irradiation time period of the radiation be a time period that is 80% of the frame time period, the omission of the change in the region to be imaged can be kept small.

Due thereto, in accordance with the present exemplary embodiment, fluoroscopic images having smooth motion can be captured.

Figure 10:
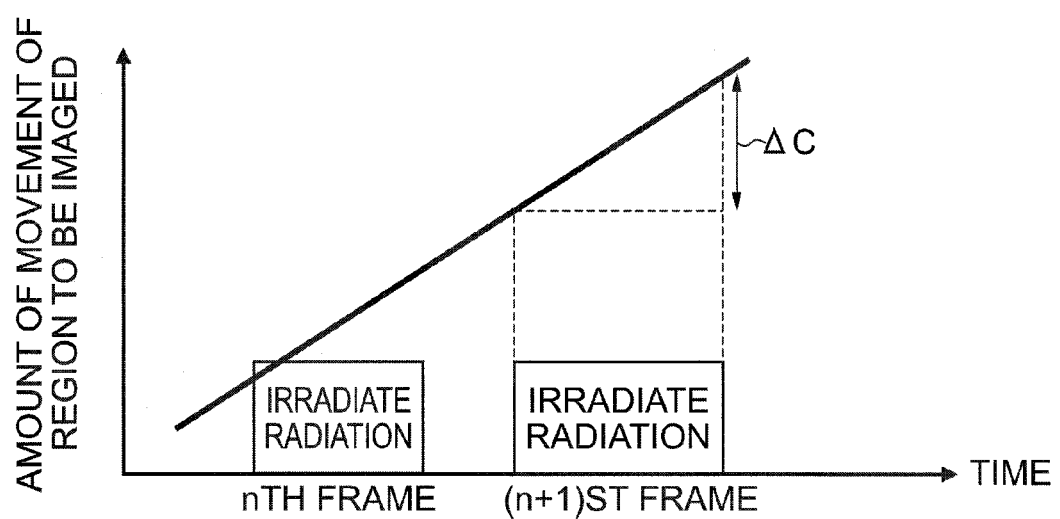
FIG. 10 is a graph showing an example of the relationship between an irradiation time period of radiation of fluoroscopic imaging relating to the first exemplary embodiment, and an amount of movement at a time when a region to be imaged moves.

If the region to be imaged moves as shown by the straight line as shown in FIG. 10, the region to be imaged moves by ΔC within each frame time period. Therefore, if the irradiation time period of the radiation is extended, the movement of the region to be imaged becomes large. If excessive blurring arises at the region to be imaged in each frame image that is fluoroscopically imaged, it is difficult to confirm the state of the region to be imaged.

Thus, at the console 42 relating to the present exemplary embodiment, during fluoroscopic imaging, the image data that are successively transmitted from the electronic cassette 32 are compared, and movement detection is carried out. Any of various known methods can be used as the movement detection method.

Further, at the console 42 relating to the present exemplary embodiment, if the detected movement amount is greater than or equal to a predetermined allowed amount, the frame rate is changed so as to be increased, the above-described irradiation time period setting processing is carried out at the changed frame rate and the irradiation time period is set, and fluoroscopic imaging is carried out at the changed frame rate.

Due thereto, in accordance with the present exemplary embodiment, in a case in which movement of the region to be imaged is great, by quickly changing the frame rate, fluoroscopic images, that are smooth and in which it is easy to view the state of the region to be imaged, can be captured.

Second Exemplary Embodiment

A second exemplary embodiment is described next.

The structures of the RIS 10, the imaging system 18, the electronic cassette 32, the radiation generating device 34, and the console 42 relating to the second exemplary embodiment are the same as those of the above-described first exemplary embodiment (see FIG. 1 through FIG. 5), and therefore, description thereof is omitted here.

In the imaging system 18 relating to the present exemplary embodiment as well, fluoroscopic imaging is carried out by pulse irradiation.

Further, in the present exemplary embodiment, a frame rate threshold value is stored in advance in the HDD 110. If the frame rate of the fluoroscopic imaging is less than or equal to the threshold value, the irradiation time period of the pulse irradiation within the frame time period is changed. In the present exemplary embodiment, two frame rate threshold values (a first frame rate threshold value and a second frame rate threshold value) are stored. It suffices for the first frame rate threshold value to be a frame rate at which the great majority of people do not sense flickering. Concretely, it suffices for the first frame rate threshold value to be greater than or equal to 15 fps (frames per second) and less than or equal to 60 fps, and greater than or equal to 15 fps and less than or equal to 30 fps is more preferable. Alternatively, in a case of imaging a rapidly moving region, for instance, that of a heart of an infant or a child, the first frame rate threshold value may be set to be greater than 15 fps and less than or equal to 120 fps. It suffices for the second frame rate threshold value to be a frame rate at which the great majority of people sense flickering. Concretely, it suffices for the second frame rate threshold value to be greater than or equal to 5 fps and less than the first frame rate threshold value, and greater than or equal to 5 fps and less than 15 fps is more preferable. In the present exemplary embodiment, the first frame rate threshold value is made to be 30 fps for example, and the second frame rate threshold value is made to be 15 fps for example. However, the first frame rate threshold value may be made to be 24 fps for example, and the second frame rate threshold value may be made to be 5 fps for example.

In the imaging system 18 relating to the present exemplary embodiment, if the frame rate of the fluoroscopic imaging is greater than the first frame rate threshold value, while radiation is pulse-irradiated at a predetermined irradiation time period, capturing of radiographic images is carried out synchronously with that pulse irradiation. The irradiation time period is set to a time at which stable imaging is possible even at the maximum frame rate at which images can be captured at the imaging system 18, and is stored in the HDD 110 as an irradiation time period initial value.

Further, in the imaging system 18 relating to the present exemplary embodiment, if the frame rate of the fluoroscopic imaging is less than or equal to the first frame rate threshold value, while radiation is pulse-irradiated with the proportion of the irradiation time period with respect to the frame time period changed to 50%, capturing of radiographic images is carried out synchronously with that pulse irradiation. If the frame rate of the fluoroscopic imaging is less than or equal to the second frame rate threshold value, while radiation is pulse-irradiated with the proportion of the irradiation time period with respect to the frame time period changed to 80%, capturing of radiographic images is carried out synchronously with that pulse irradiation.

Figure 11:
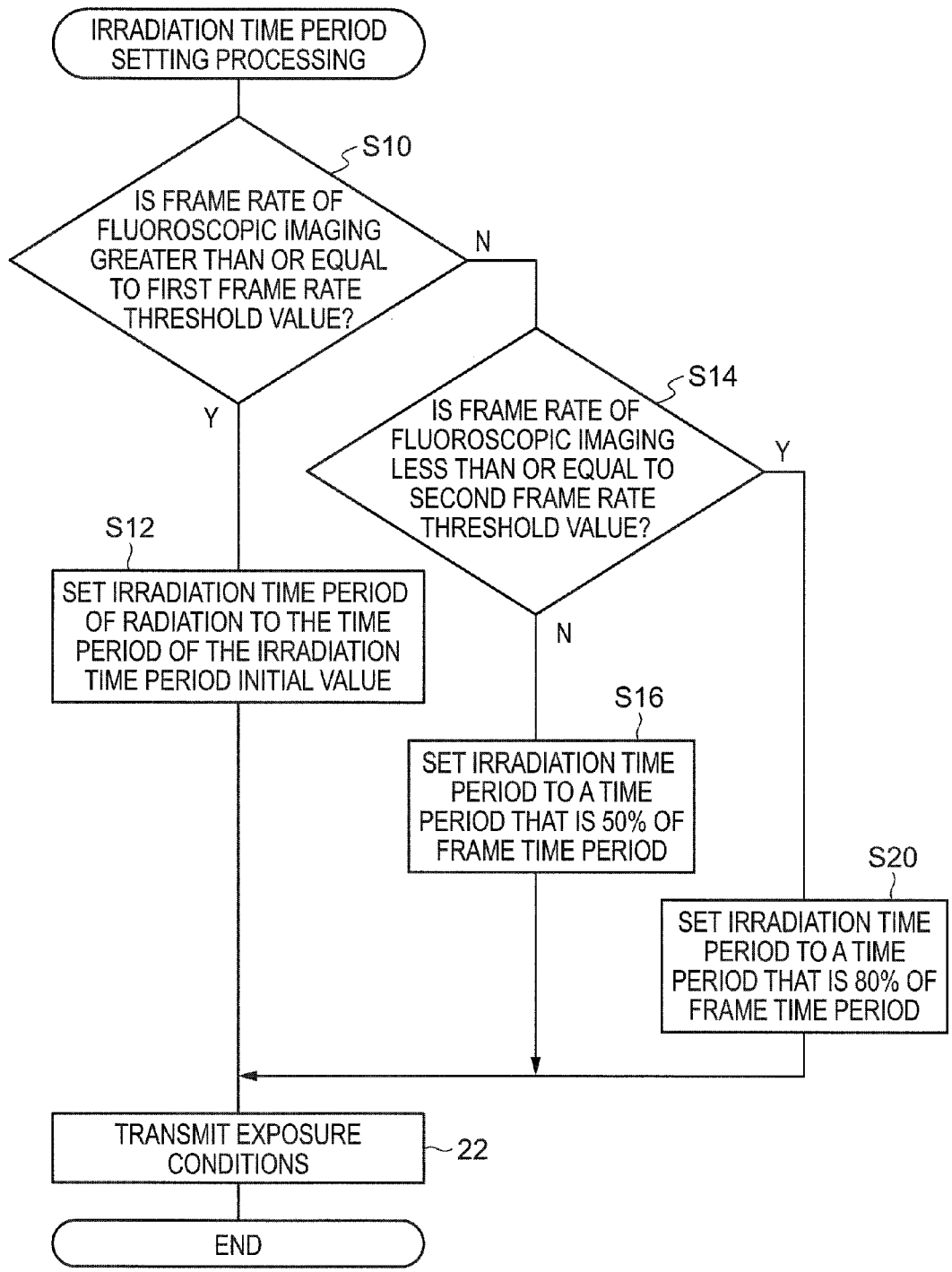
FIG. 11 is a flowchart showing the flow of processings of an irradiation time period setting processing program relating to a second exemplary embodiment.

A flowchart showing the flow of processings of an irradiation time period setting processing program, that is executed by the CPU 104 relating to the second exemplary embodiment, is shown in FIG. 11.

In step S10 of FIG. 11, the CPU 104 judges whether or not the frame rate of the fluoroscopic imaging is greater than or equal to the first frame rate threshold value (e.g., 30 fps). If the judgment is affirmative, the routine moves on to step S12, whereas if the judgment is negative, the routine moves on to step S14.

In step S12, the CPU 104 sets the irradiation time period of radiation in each pulse irradiation to a time period expressed by the irradiation time period initial value.

On the other hand, in step S14, the CPU 104 judges whether or not the frame rate of the fluoroscopic imaging is less than or equal to the second frame rate threshold value (e.g., 15 fps). If the judgment is affirmative, the routine moves on to step S20, whereas if the judgment is negative, the routine moves on to step S16.

In step S16, the CPU 104 sets the irradiation time period of radiation in each pulse irradiation to a time period that is 50% of the frame time period that corresponds to the designated frame rate. Further, accompanying the change to the irradiation time period, the CPU 104 also changes the exposure conditions, such as the tube voltage, the tube current and the like, so as to lower the irradiated amount of the radiation per unit time.

On the other hand, in step S20, the CPU 104 sets the irradiation time period of radiation in each pulse irradiation to a time period that is 80% of the frame time period that corresponds to the designated frame rate. Further, accompanying the change to the irradiation time period, the CPU 104 also changes the exposure conditions, such as the tube voltage, the tube current and the like, so as to lower the irradiated amount of the radiation per unit time.

In step S22, the CPU 104 transmits the set irradiation time period, and the designated frame rate, tube voltage, tube current and the like as exposure conditions to the electronic cassette 32 and the radiation generating device 34, and ends the present irradiation time period setting processing program.

Due thereto, in accordance with the present exemplary embodiment, fluoroscopic images having smooth motion can be captured even in cases in which the frame rate of the fluoroscopic imaging is low.

Third Exemplary Embodiment

A third exemplary embodiment is described next.

The structures of the RIS 10, the imaging system 18, the electronic cassette 32, the radiation generating device 34, and the console 42 relating to the third exemplary embodiment are the same as those of the above-described first exemplary embodiment (see FIG. 1 through FIG. 5), and therefore, description thereof is omitted here.

Here, in the fluoroscopic imaging, even in cases in which the frame rate is low, if the region to be imaged that is the object of imaging is stationary or the movement thereof is slow, the captured images are easy to view as video images. If the moved amount of the region to be imaged that is the object of imaging is great, it is difficult to view the captured images as video images.

Thus, at the console 42 relating to the present exemplary embodiment, even in cases in which the frame rate is low, the irradiation time period of radiation in each pulse irradiation is set to be a time period that is expressed by the irradiation time period initial value, and fluoroscopic imaging is carried out.

Further, at the console 42, a threshold value of a movement amount at which it becomes difficult to view the captured images as video images is stored in advance in the HDD 110. During fluoroscopic imaging, the image data that are transmitted successively from the electronic cassette 32 are compared, and movement detection is carried out. If the detected movement amount is greater than or equal to the aforementioned threshold value, the irradiation time period with respect to the frame time period is extended. This extending of the irradiation time period is carried out such that the proportion of the irradiation time period with respect to the frame time period is made to be within the range of 12.5 to 80%, and more preferably, is made to be within the range of 33 to 80%. In the present exemplary embodiment, the proportion of the irradiation time period with respect to the frame time period is extended to 80%.

Figure 12:
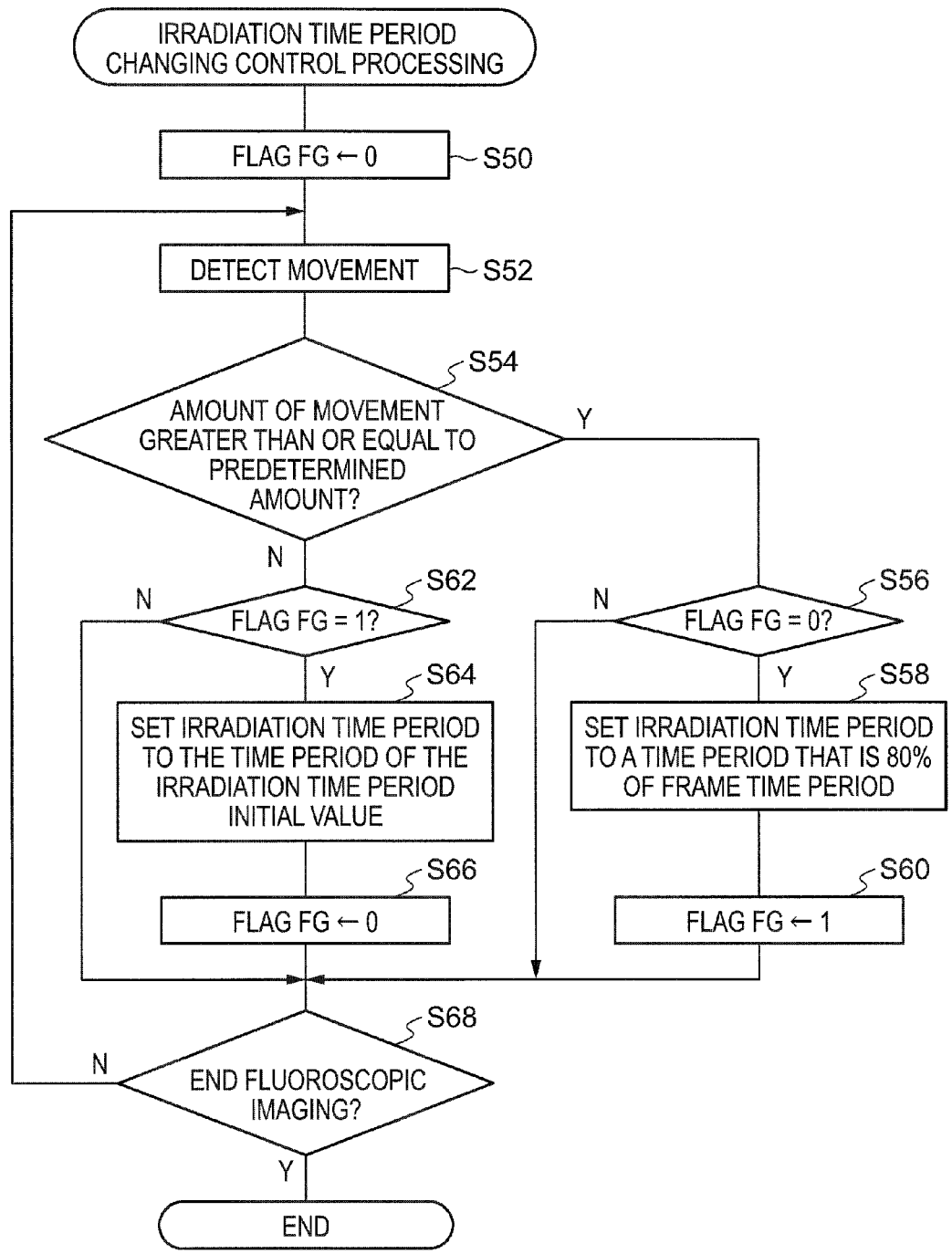
FIG. 12 is a flowchart showing the flow of processings of an irradiation time period changing control processing program relating to a third exemplary embodiment.

A flowchart showing the flow of processings of an irradiation time period changing control processing program, that is executed by the CPU 104 relating to the third exemplary embodiment, is shown in FIG. 12. Note that this program is stored in advance in a predetermined area of the HDD 110, and is executed at the time when fluoroscopic imaging is started.

In step S50 of FIG. 12, the CPU 104 initializes, to zero, the value stored at flag FG.

In next step S52, the CPU 104 compares the image data that are successively transmitted from the electronic cassette 32, and carries out movement detection.

In subsequent step S54, the CPU 104 judges whether or not the movement amount detected in above step S52 is greater than or equal to a predetermined amount. If the judgment is affirmative, the routine moves on to step S56, whereas if the judgment is negative, the routine moves on to step S62.

In step S56, the CPU 104 judges whether or not the value stored at the flag FG is zero. If the judgment is affirmative, the routine moves on to step S58, whereas if the judgment is negative, the routine moves on to step S68.

In step S58, the CPU 104 changes the proportion of the irradiation time period with respect to the frame time period to 80%. Further, accompanying the change to the irradiation time period, the CPU 104 also changes the exposure conditions, such as the tube voltage, the tube current and the like, so as to lower the irradiated amount of radiation per unit time. Then, the CPU 104 transmits the changed exposure conditions to the electronic cassette 32 and the radiation generating device 34.

In step S60, the CPU 104 updates the value stored at the flag FG to 1.

On the other hand, in step S62, the CPU 104 judges whether or not the value stored at the flag FG is 1. If the judgment is affirmative, the routine moves on to step S64, whereas if the judgment is negative, the routine moves on to step S68.

In step S64, the CPU 104 changes the irradiation time period to the time period expressed by the irradiation time period initial value, and changes the tube voltage and the tube current to the initial exposure conditions that the operator 50 designated at the operation panel 102, and transmits the changed exposure conditions to the electronic cassette 32 and the radiation generating device 34.

In step S66, the CPU 104 updates the value stored at the flag FG to zero.

In step S68, the CPU 104 judges whether or not the fluoroscopic imaging is finished. If this judgment is affirmative, the CPU 104 ends the present irradiation time period changing control processing program. If the judgment is negative, the routine moves on to step S52.

Figure 13:
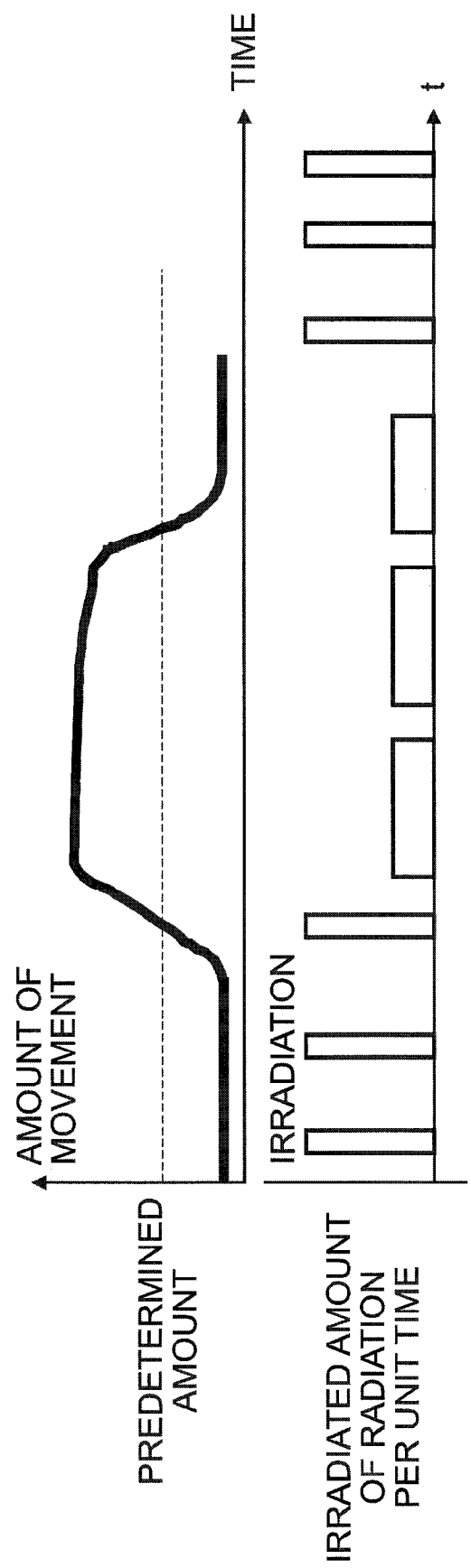
FIG. 13 is a graph showing an example of an amount of movement of a region to be imaged and changing of an irradiation time period relating to the third exemplary embodiment.

In this way, in accordance with the present exemplary embodiment, as shown in FIG. 13, the irradiation time period is extended in a case in which the amount of movement of the region to be imaged is greater than or equal to a predetermined amount. Therefore, fluoroscopic images, that are smooth and in which it is easy to view the state of the region to be imaged, can be captured.

Fourth Exemplary Embodiment

A fourth exemplary embodiment is described next.

The structures of the RIS 10, the imaging system 18, the electronic cassette 32, the radiation generating device 34, and the console 42 relating to the fourth exemplary embodiment are the same as those of the above-described first exemplary embodiment (see FIG. 1 through FIG. 5), and therefore, description thereof is omitted here.

At the console 42 relating to the present exemplary embodiment, even in cases in which the frame rate is low, the irradiation time period of radiation in each pulse irradiation is set to a time period that is expressed by an irradiation time period initial value, and fluoroscopic imaging is carried out.

Further, in the imaging system 18 relating to the present exemplary embodiment, still imaging during fluoroscopic imaging is possible.

In order to observe, in detail, the interior of the region to be imaged, it is preferable that the image quality of the still imaging be high. Therefore, in the still imaging, imaging is carried out by irradiating a greater irradiated amount of radiation per unit time than in fluoroscopic imaging.

Figure 14A:
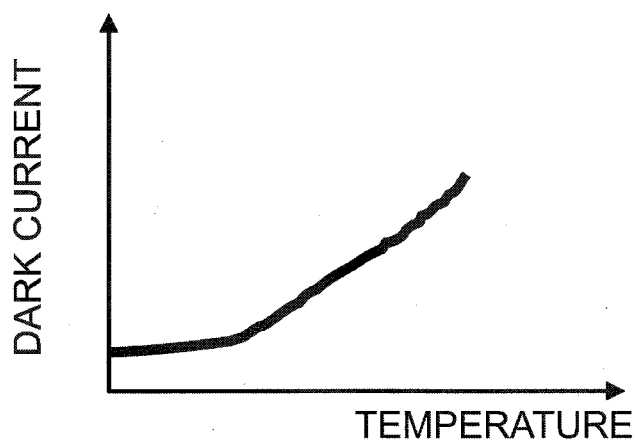
FIG. 14A is a graph showing the relationship between temperature and dark current amount.
Figure 14B:
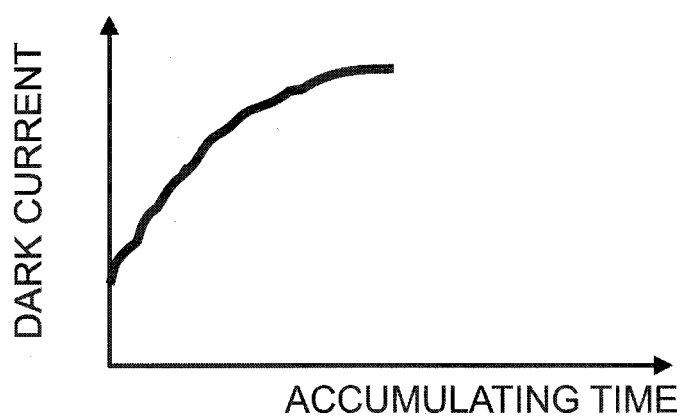
FIG. 14B is a graph showing the relationship between accumulation time and dark current amount.

On the other hand, at the radiation detector 60, even in the state in which charges become trapped within the sensor portions 72 and X-rays are not being irradiated, charges are generated at the sensor portions 72 by dark current and the like, and the charges are accumulated in the storage capacitors 68 of the respective pixel portions 74. The greater the irradiated radiation amount per unit time, the more that the amount of dark current that is generated at the radiation detector 60 increases. Further, as shown in FIG. 14A, the higher the temperature, the more that the amount of dark current that is generated at the radiation detector 60 increases. Moreover, as shown in FIG. 14B, the amount of dark current that is generated at the radiation detector 60 increases in accordance with the accumulating time, but when the accumulating time becomes long, the trapped charges are released, and therefore, the amount of increase decreases.

Therefore, in a case of carrying out still imaging during fluoroscopic imaging, the irradiated radiation amount per unit time becomes great, and the charges trapped within the sensor portions 72 also become great. Therefore, the amount of noise becomes great in the respective frame images of the fluoroscopic imaging immediately after the still imaging.

Thus, in a case of carrying out still imaging during fluoroscopic imaging, the console 42 extends the irradiation time period with respect to the frame time period. This extending of the irradiation time period is carried out such that the proportion of the irradiation time period with respect to the frame time period is made to be within the range of 12.5 to 80%, and more preferably, is made to be within the range of 33 to 80%. In the present exemplary embodiment, the proportion of the irradiation time period with respect to the frame time period is extended to 80%.

Figure 15:
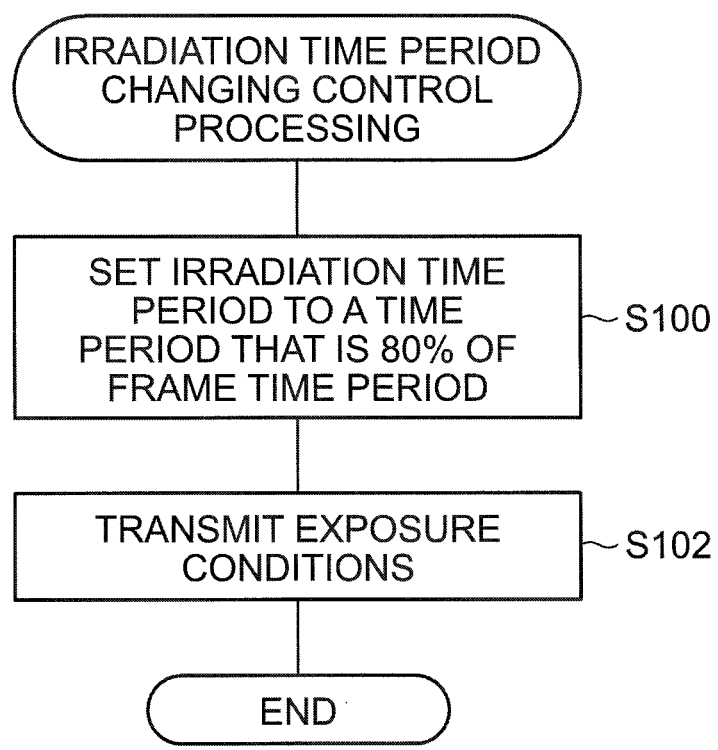
FIG. 15 is a flowchart showing the flow of processings of an irradiation time period changing control processing program relating to a fourth exemplary embodiment.

A flowchart showing the flow of processings of an irradiation time period changing control processing program, that is executed by the CPU 104 relating to the fourth exemplary embodiment, is shown in FIG. 15. Note that this program is stored in advance in a predetermined area of the HDD 110, and is executed at the time when still imaging is carried out during fluoroscopic imaging.

In step S100 of FIG. 15, the CPU 104 changes the proportion of the irradiation time period with respect to the frame time period to 80%.

In next step S102, the CPU 104 transmits the exposure conditions, that were changed in above step S100, to the electronic cassette 32 and the radiation generating device 34, and ends the present fluoroscopic imaging irradiation time period changing control processing program.

Figure 16:
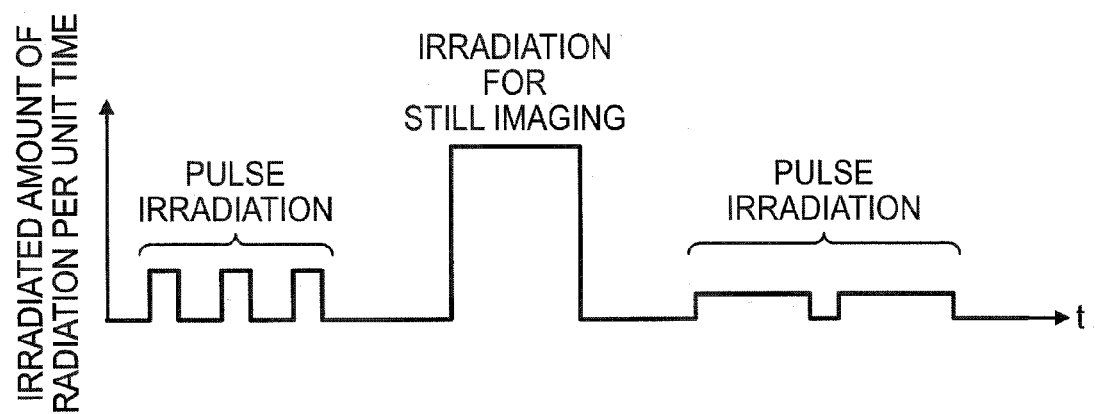
FIG. 16 is a time chart showing the flow of image capturing operations relating to the fourth exemplary embodiment.

A time chart showing the flow of image capturing operations at the time of carrying out still imaging during fluoroscopic imaging is shown in FIG. 16.

Due thereto, in accordance with the present exemplary embodiment, in a case in which movement of the region to be imaged is great, the irradiation time period is extended. Fluoroscopic images, that are smooth and in which it is easy to view the state of the region to be imaged, can thereby be captured.

Fifth Exemplary Embodiment

A fifth exemplary embodiment is described next.

The structures of the RIS 10, the imaging system 18, the radiation generating device 34, and the console 42 relating to the fifth exemplary embodiment are the same as those of the above-described first exemplary embodiment (see FIG. 1 through FIG. 5), and therefore, description thereof is omitted here.

Figure 17:
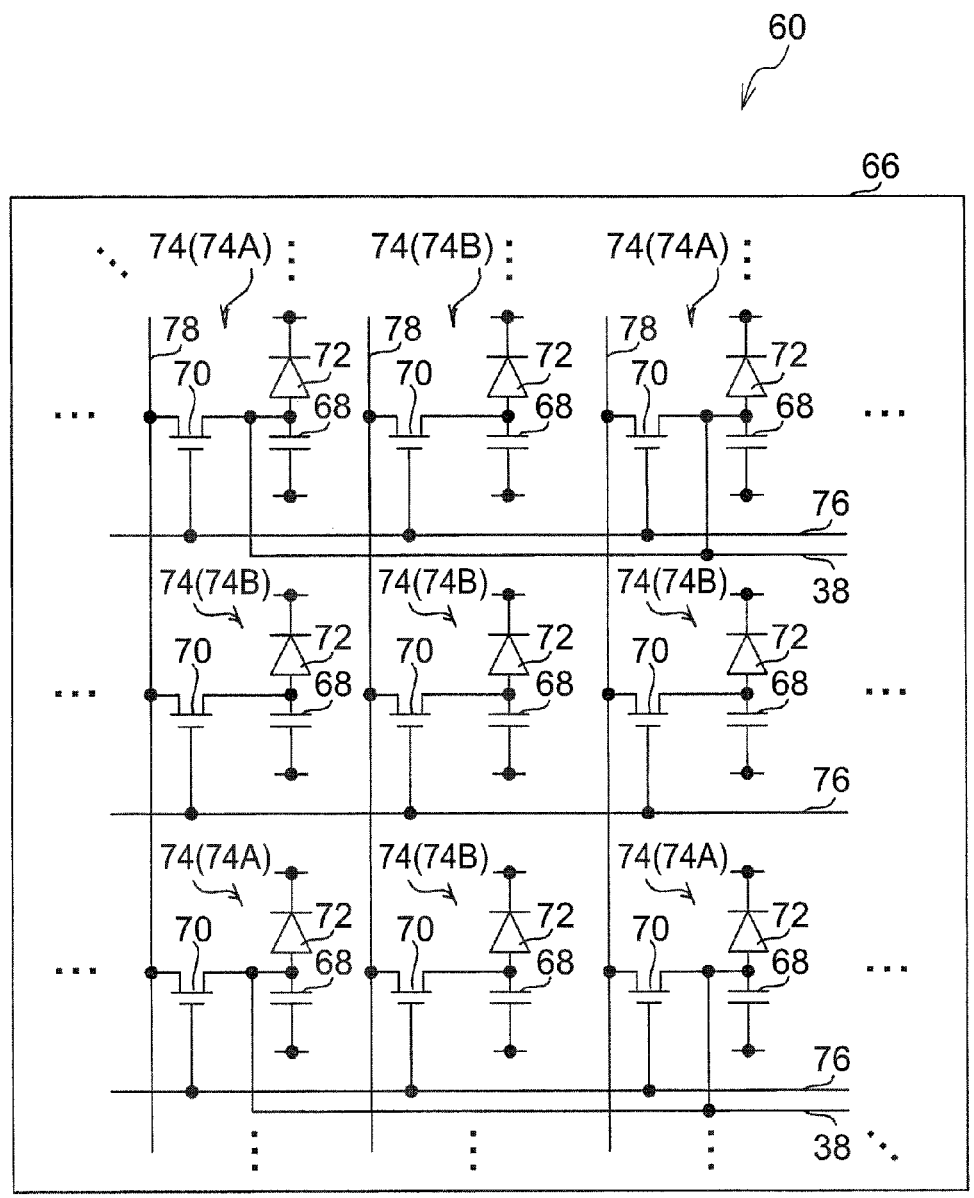
FIG. 17 is a plan view showing the structure of a radiation detector relating to a fifth exemplary embodiment.

A plan view showing the structure of the radiation detector 60 relating to the present exemplary embodiment is shown in FIG. 17.

At the TFT active matrix substrate 66 of the radiation detector 60, the plural pixel portions 74, that are each structured to include the sensor portion 72, the storage capacitor 68 and the TFT 70, are provided in a two-dimensional form in a given direction (the row direction in FIG. 17) and in a direction (the column direction in FIG. 17) intersecting the given direction.

Further, the plural gate lines 76, that extend in the aforementioned given direction (the row direction) and are for turning the respective TFTs 70 on and off, and the plural data lines 78, that extend in the aforementioned intersecting direction (the column direction) and are for reading-out charges via the TFTs 70 that are in an on state, are provided at the radiation detector 60.

The radiation detector 60 is flat-plate-shaped, and, in plan view, is shaped as a quadrilateral having four sides at the outer edge thereof. More concretely, the radiation detector 60 is rectangular.

Here, in the radiation detector 60 relating to the present exemplary embodiment, some of the pixel portions 74 are used in order to detect the irradiated state of radiation, and capturing of radiographic images is carried out by the remaining pixel portions 74. Note that, hereinafter, the pixel portions 74 for detecting the irradiated state of the radiation are called pixel portions 74A for radiation detection (irradiation detecting unit), and the remaining pixel portions 74 are called pixel portions 74B for radiographic image acquisition.

In the radiation detector 60 relating to the present exemplary embodiment, capturing of a radiographic image is carried out by, of the pixel portions 74, the pixel portions 74B for radiographic image acquisition excluding the pixel portions 74A for radiation detection. Therefore, pixel data of a radiographic image at the positions where the pixel portions 74A for radiation detection are disposed cannot be obtained. Therefore, in the present exemplary embodiment, the pixel portions 74A for radiation detection are disposed so as to be scattered. The pixel data of the radiographic image at the positions where the pixel portions 74A for radiation detection are disposed, is generated by interpolation by using the pixel data acquired by the pixel portions 74B for radiographic image acquisition that are positioned at the peripheries of these pixel portions 74A for radiation detection.

As shown in FIG. 17, direct read-out lines 38 are provided at the radiation detector 60 relating to the present exemplary embodiment so as to extend in the aforementioned given direction (the row direction). The connected portions of the storage capacitors 68 and the TFTs 70 at the pixel portions 74A for radiation detection are connected to the direct read-out lines 38, and the direct read-out lines 38 are for directly reading-out the charges accumulated in these storage capacitors 68. Note that, in the radiation detector 60 relating to the present exemplary embodiment, one of the direct read-out lines 38 is assigned to plural pixel portions 74A for radiation detection that are lined-up in the aforementioned given direction, and the connected portions of the storage capacitors 68 and the TFTs 70 at these plural pixel portions 74A for radiation detection are connected to the common (single) direct read-out line 38.

The structures of the main portions of the electrical system of the electronic cassette 32 relating to the present exemplary embodiment are described next with reference to FIG. 18.

Figure 18:
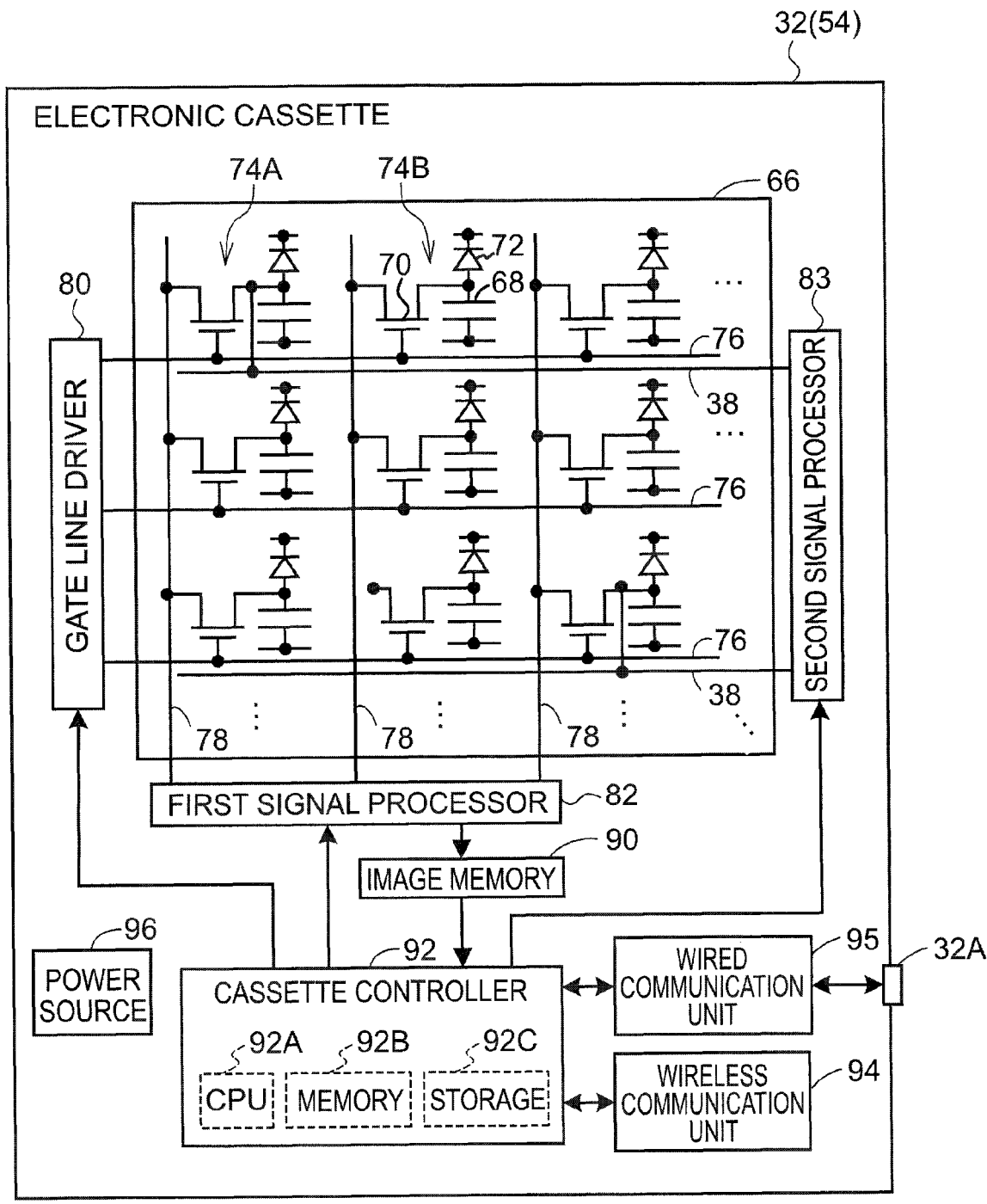
FIG. 18 is a block diagram showing the structures of main portions of the electrical system of an electronic cassette relating to the fifth exemplary embodiment.

As shown in FIG. 18, at the radiation detector 60 that is incorporated within the electronic cassette 32, the gate line driver 80 is disposed at one side of two adjacent sides, and the signal processor 82 (hereinafter the "signal processor 82" is called a "first signal processor 82") is disposed at the other side. The individual gate lines 76 of the TFT active matrix substrate 66 are connected to the gate line driver 80, and the individual data lines 78 of the TFT active matrix substrate 66 are connected to the first signal processor 82.

The respective TFTs 70 of the TFT active matrix substrate 66 are turned on in order in units of rows by signals supplied from the gate line driver 80 via the gate lines 76, and the charges, that are read-out by the TFTs 70 that have been turned on, are transferred through the data lines 78 as electrical signals and are inputted to the first signal processor 82. Due thereto, the charges are read-out in order in units of rows, and a two-dimensional radiographic image can be acquired.

Further, at the electronic cassette 32, a second signal processor 83 (irradiation detecting unit) is disposed at the side opposite the gate line driver 80, with the TFT active matrix substrate 66 therebetween. The individual direct read-out lines 38 of the TFT active matrix substrate 66 are connected to the second signal processor 83.

The second signal processor 83 has amplifiers and A/D converters that are provided for each of the direct read-out lines 38, and is connected to the cassette controller 92. Due to control from the cassette controller 92, the second signal processor 83 carries out sampling of the respective direct read-out lines 38 at a predetermined cycle, and converts the electrical signals that are transferred through the respective direct read-out lines 38 into digital data, and successively outputs the converted digital data to the cassette controller 92.

Operation of the imaging system 18 relating to the present exemplary embodiment is described next.

At the console 42 relating to the present exemplary embodiment, in the same way as in the first exemplary embodiment, the irradiation time period of the radiation is changed to a time period that is 80% of the frame time period. Further, accompanying the changing of the irradiation time period, the exposure conditions such as the tube voltage, the tube current, and the like, also are changed so as to lower the irradiated amount of radiation per unit time, and fluoroscopic imaging is carried out.

At the electronic cassette 32 relating to the present exemplary embodiment, sampling of the electrical signals, that have flowed-out from the pixel portions 74A for radiation detection to the respective direct read-out lines 38, is carried out by the second signal processor 83, and the electrical signals are converted into digital data. On the basis of the converted digital data, starting of irradiation of radiation is detected. The radiographic image capturing operations are started at the time when irradiation of the radiation starts. Namely, the electronic cassette 32 detects irradiation of the radiation, and starts the image capturing operations. Due thereto, in the imaging system 18 relating to the present exemplary embodiment, a radiographic image can be captured even without synchronizing the operation of irradiating radiation from the radiation generating device 34 and the image capturing operation at the electronic cassette 32 by carrying out transmitting and receiving of data relating to the start of irradiating of the radiation between the console 42 or the radiation generating device 34 and the electronic cassette 32.

Figure 19:
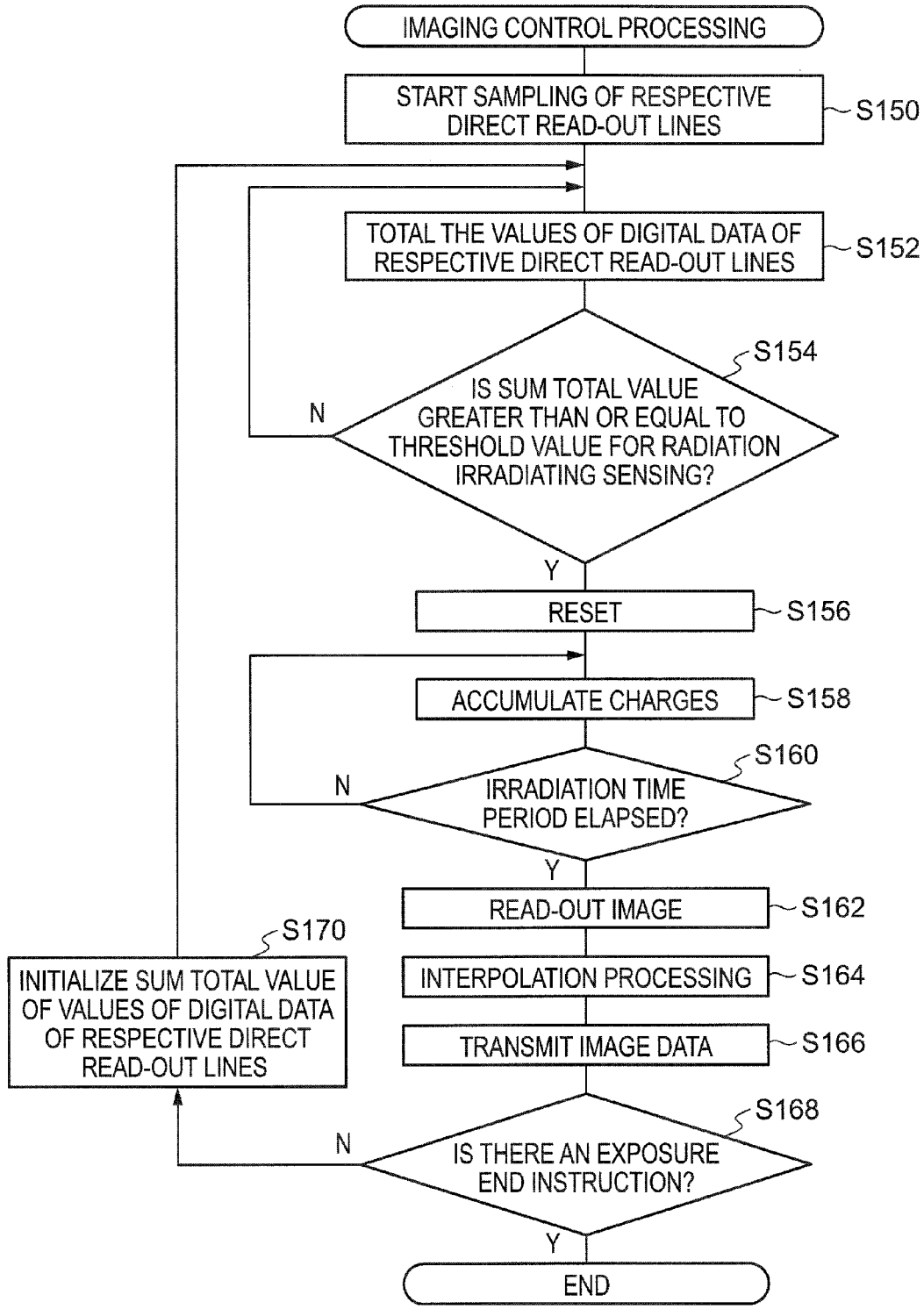
FIG. 19 is a flowchart showing the flow of processings of an imaging control processing program relating to the fifth exemplary embodiment.

A flowchart showing the flow of the processings of an imaging control processing program, that is executed by the CPU 92A of the cassette controller 92 at the time when imaging conditions and exposure conditions are received from the console 42, is shown in FIG. 19. Note that this program is stored in advance in a predetermined area of the memory 92B (ROM).

In step S150 of FIG. 19, the CPU 92A causes sampling of the respective direct read-out lines 38 to be started by the second signal processor 83.

Due thereto, the second signal processor 83 samples the respective direct read-out lines 38 at a predetermined cycle, and converts the electrical signals that are transmitted through the respective direct read-out lines 38 into digital data, and successively outputs the converted digital data to the cassette controller 92.

In next step S152, by totaling the values of the digital data of the respective direct read-out lines 38 that are inputted from the second signal processor 83, the CPU 92A determines a total amount of radiation irradiated from the radiation source.

In next step S154, the CPU 92A compares the sum total value that was totaled in above step 152 and a predetermined threshold value for radiation irradiation sensing, and carries out detection of the start of irradiation of the radiation in accordance with whether or not the sum total value is greater than or equal to the threshold value for radiation irradiation sensing. If the sum total value is greater than or equal to the threshold value for radiation irradiation sensing, it is considered that irradiation of radiation has started and the routine moves on to step S156. If the sum total value is less than the threshold value for radiation irradiation sensing, the routine moves to step S152 again, and awaits the start of irradiation of radiation.

In step S156, the CPU 92A carries out a resetting operation of controlling the gate line driver 80 to cause control signals for turning the TFTs 70 on to be outputted in order from the gate line driver 80 to the respective gate lines 76.

Due thereto, at the radiation detector 60, the charges accumulated in the storage capacitors 68 of the respective pixel portions 74 flow-out in order and line-by-line to the respective data lines 78 as electrical signals, and the charges, that have been accumulated in the storage capacitors 68 of the respective pixel portions 74 due to dark current or the like, are removed.

In next step S158, the CPU 92A controls the gate line driver 80 to cause control signals, that turn off the TFTs 70 of the respective pixel portions 74, to be outputted from the gate line driver 80 to the respective gate lines 76. Due thereto, charges corresponding to the irradiated radiation amount are accumulated in the respective pixel portions 74.

In subsequent step S160, the CPU 92A judges whether or not the irradiation time period, that is expressed by the exposure conditions, has elapsed from the point in time when the start of irradiation of radiation was detected in above step S152. If this judgment is affirmative, the routine moves on to step S162, whereas if the judgment is negative, the routine moves on again to step S158.

In step S162, the CPU 92A controls the gate line driver 80 to cause on signals to be outputted from the gate line driver 80 to the respective gate lines 76 in order and line-by-line.

At the radiation detector 60, when on signals are inputted to the respective gate lines 76, the TFTs 70 of the respective pixel portions 74 that are connected to the respective gate lines 76 are turned on in order and line-by-line. The charges accumulated in the storage capacitors 68 of the respective pixel portions 74 flow-out, in order and line-by-line, to the respective data lines 78 as electrical signals. The electrical signals that have flowed-out to the respective data lines 78 are converted into digital image data at the first signal processor 82, and are stored in the image memory 90. Due thereto, image data, that expresses a radiographic image captured by the respective pixel portions 74A for radiation detection of the radiation detector 60, is stored in the image memory 90.

At the radiation detector 60 relating to the present exemplary embodiment, the pixel portions 74A for radiation detection are provided together with the pixel portions 74B for radiographic image acquisition. The charges generated at the pixel portions 74A for radiation detection flow-out to the direct read-out lines 38. Therefore, in the radiographic image that is expressed by the image data, the pixels corresponding to the pixel portions 74A for radiation detection become defective pixels.

Thus, in step S164, the CPU 92A carries out interpolation processing on the radiographic image stored in the image memory 90, and generates data of the respective pixels corresponding to the respective pixel portions 74A for radiation detection, by interpolation from the data of the pixel portions 74B for radiographic image acquisition at the peripheries of the respective pixel portions 74A for radiation detection.

In next step S166, the CPU 92A transmits, to the console 42, the image data of the radiographic image that was subjected to interpolation processing in above step S164.

In subsequent step S168, the CPU 92A judges whether or not instruction data that instructs the ending of exposure has been received from the console 42. If this judgment is affirmative, the present imaging control processing program ends. If the judgment is negative, the routine moves on to step S170.

In step S170, the CPU 92A initializes the sum total value of the digital data of the respective direct read-out lines 38 to zero, and the routine moves on to step S152.

Figure 20A:
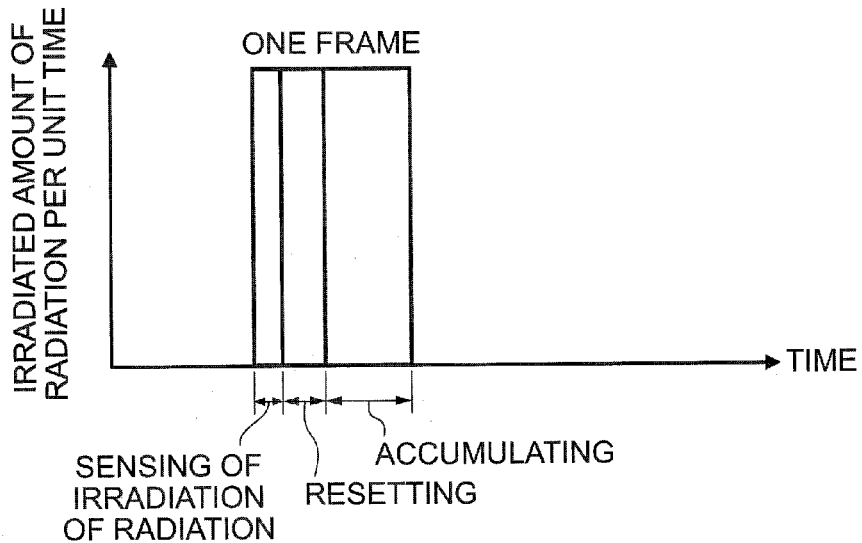
FIG. 20A is a graph showing an example of radiation sensing, resetting, and charge accumulating time periods per one frame in conventional fluoroscopic imaging.

Here, in conventional fluoroscopic imaging, for example, fluoroscopic imaging is carried out by carrying out pulse irradiation with the irradiation time period of the radiation being a relatively short time period, as shown in FIG. 20A. In the present exemplary embodiment, in a case in which the start of irradiation of radiation is detected, a resetting operation is carried out, and the charges accumulated in the storage capacitors 68 of the respective pixel portions 74 due to dark current and the like are removed, and thereafter, accumulation is started. However, the radiation that is irradiated during the resetting operation is wasted.

Figure 20B:
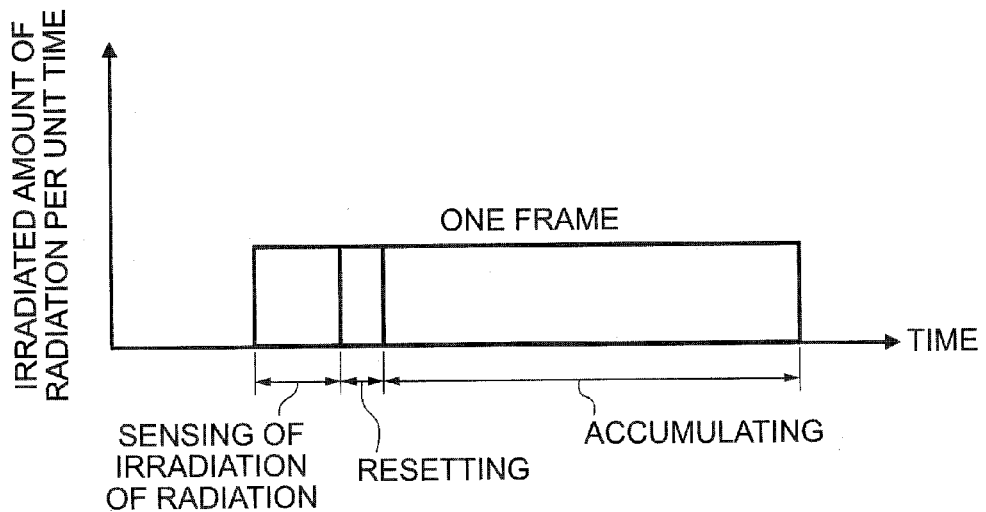
FIG. 20B is a graph showing an example of radiation sensing, resetting, and charge accumulating time periods per one frame in fluoroscopic imaging relating to the fifth exemplary embodiment.

On the other hand, in the present exemplary embodiment, as shown in FIG. 20B, the irradiation time period of the radiation is changed, and the irradiated amount of radiation per unit time is reduced. Therefore, the amount of radiation that is irradiated during the resetting operation and is wasted can be kept small.

The present invention has been described by using exemplary embodiments, but the technical scope of the present invention is not limited to the ranges described in the above exemplary embodiments. Various changes and improvements can be made to the exemplary embodiments within a range that does not deviate from the gist of the present invention, and forms to which such changes or improvements are made also are included within the technical scope of the present invention.

Figure 21A:
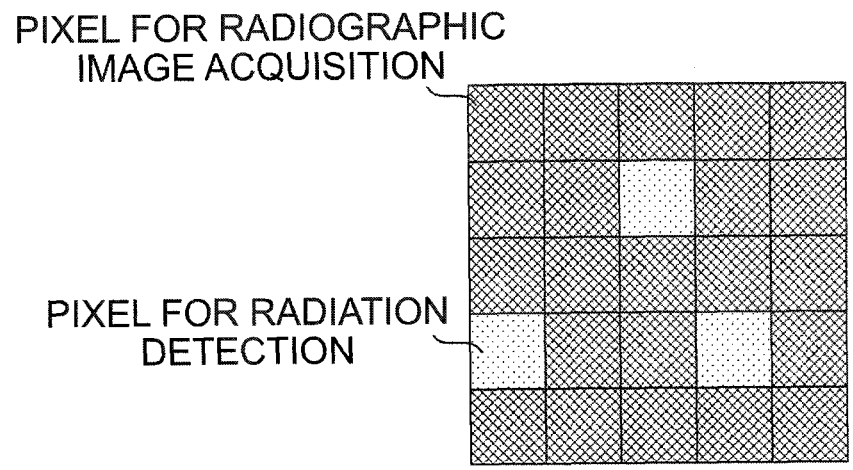
FIG. 21A is a plan view showing an example of the structure of a radiation detector relating to another form.
Figure 21B:
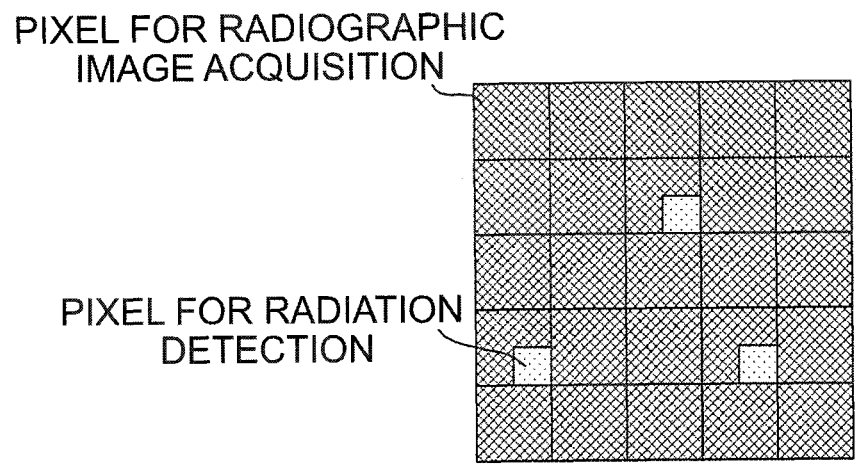
FIG. 21B is a plan view showing an example of the structure of a radiation detector relating to another form.

Further, the fifth exemplary embodiment describes, as an example, a case in which some of the pixel portions 74B for radiographic image acquisition are used as the pixel portions 74A for radiation detection, as shown in FIG. 21A. However, the present invention is not limited to the same. For example, as shown as an example in FIG. 21B, there may be a form in which the pixel portions 74A for radiation detection are provided at gaps of the pixel portions 74B for radiographic image acquisition. In this case, the surface area of the pixel portions 74B for radiographic image acquisition, that correspond to the positions at which the pixel portions 74A for radiation detection are provided, becomes smaller. Therefore, these pixels as well can be used for radiographic image detection even though the sensitivity of these pixels is reduced. Thus, the quality of the radiographic image can be improved.

Further, the above exemplary embodiments describe a case in which some of the pixel portions 74 that are provided at the radiation detector 60 are used as the pixel portions 74A for radiation detection, but the present invention is not limited to the same. For example, there may be a form in which the pixel portions 74A for radiation detection are layered on the radiation detector 60 as a layer separate from the pixel portions 74, and are made to be a radiation detecting unit. In this case, because no defective pixels arise, the quality of the radiographic image can be improved as compared with the above-described exemplary embodiment. Further, the pixel portions 74A for radiation detection and the radiation detecting unit may respectively be structured so as to individually read-out the charges.

Moreover, the above exemplary embodiments describe a case in which reading-out of the charges from the radiation detector 60 is carried out at the point in time when the irradiation time period expressed by the exposure conditions has elapsed from the point in time that the start of irradiation of radiation is detected. However, the present invention is not limited to the same. For example, even from the detection of the start of irradiation of radiation and thereon, comparison of the value of the digital data of the direct read-out line 38, that has become greater than or equal to the threshold value for radiation irradiation sensing, with the threshold value for radiation irradiation sensing may be continued, and the reading-out of charges from the radiation detector 60 may be carried out by considering that the irradiation of the radiation ended at the point in time when the value of the digital data of that direct read-out line 38 became less than the threshold value for radiation irradiation sensing.

Further, the above third exemplary embodiment describes a case in which, if the amount of movement of the region to be imaged is greater than or equal to a threshold value, the irradiation time period with respect to the frame time period is extended. However, the present invention is not limited to the same. For example, region data, that expresses a predetermined region at which the movement of the region to be imaged is rapid, such as the heart or the like, may be stored in advance in the HDD 110, and, at the time of imaging, the region to be imaged may be designated by the operator through the operation panel 102, and, if the designated region to be imaged is a predetermined region at which movement is rapid, extending of the irradiation time period with respect to the frame time period may be carried out.

Further, although the above exemplary embodiments describe cases in which X-rays are used as the radiation, the present invention is not limited to the same, and may be made to be a form that uses another type of radiation such as γ-rays or the like.

In addition, the structure of the RIS 10 (see FIG. 1), the structures of the radiographic imaging room and the radiation generating device 34 (see FIG. 2), the structure of the electronic cassette 32 (see FIG. 3), and the structure of the imaging system 18 (see FIG. 4) that are described in the above exemplary embodiments are examples. Unnecessary portions may be deleted therefrom, new portions may be added thereto, and the states of connection and the like may changed within a scope that does not deviate from the gist of the present invention.

Further, the flows of the processings of the various types of programs described in the above exemplary embodiments (refer to FIG. 7, FIG. 11, FIG. 12, FIG. 15 and FIG. 19) also are examples. Unnecessary steps thereof may be deleted therefrom, new steps may be added thereto, or the order of the processings thereof may be rearranged within a scope that does not deviate from the gist of the present invention.

In the radiographic imaging system according to the first aspect of the present invention, the controller may control the radiation irradiating device such that radiation is pulse-irradiated with the proportion of the irradiation time period of radiation with respect to each frame time period being set within a range of 33% to 80%.

In the radiographic imaging system according to the first aspect of the present invention, the controller may control the radiation irradiating device such that the irradiation time period of radiation in each frame time period is extended, and the proportion of the irradiation time period of radiation with respect to each frame time period falls within the range.

In the radiographic imaging system according to the first aspect of the present invention, the controller may control the radiation irradiating device such that, in a case in which a frame rate of fluoroscopic imaging is less than or equal to a first frame rate threshold value, radiation is pulse-irradiated with the proportion of the irradiation time period with respect to each frame time period being set within a range of 12.5% to 80%, and, in a case in which the frame rate of fluoroscopic imaging is less than or equal to a second frame rate threshold value that is lower than the first frame rate threshold value, radiation is pulse-irradiated with the proportion of the irradiation time period with respect to each frame time period being set within a range of 33% to 80%.

In the radiographic imaging system according to the above aspect, the first frame rate threshold value is greater than or equal to 15 fps and less than or equal to 120 fps, and the second frame rate threshold value is greater than or equal to 5 fps and less than the first frame rate threshold value.

The radiographic imaging system according to the first aspect of the invention may further include: a movement detecting unit that detects movement of a region to be imaged, wherein, in a case in which an amount of movement detected by the movement detecting unit is greater than or equal to a predetermined threshold value, the controller may control the radiation irradiating device such that the proportion of the irradiation time period of radiation with respect to each frame time period falls within the range.

In the radiographic imaging system according to the first aspect of the invention, in a case in which a region to be imaged is a predetermined region, the controller may control the radiation irradiating device such that the proportion of the irradiation time period of radiation with respect to each frame time period falls within the range.

The radiographic imaging system according to the first aspect of the invention may further include: a storage unit, wherein, the predetermined region may be a region that is pre-designated as a region at which the movement of the region to be imaged is rapid and whose region data is stored in advance in the storage unit In the radiographic imaging system according to the first aspect of the invention, the radiographic imaging device is configured to perform still imaging during fluoroscopic imaging, and in a case in which still imaging is carried out during fluoroscopic imaging, the controller may control the radiation irradiating device such that the proportion of the irradiation time period of radiation with respect to each frame time period, in fluoroscopic imaging after still imaging, falls within the range.

In the radiographic imaging system according to the first aspect of the invention, the radiographic imaging device may include an irradiation detecting unit that detects irradiation of radiation, and, when irradiation of radiation is detected by the irradiation detecting unit, the controller may control the radiographic imaging device to carry out capturing of radiographic images after a resetting operation, that removes charges accumulated due to dark current.

A radiographic imaging system according to the second aspect of the invention includes: a radiographic imaging device that is configured to perform fluoroscopic imaging comprising continuous capture of radiographic images; a radiation irradiating device that irradiates radiation in pulse form with respect to the radiographic imaging device at a time of fluoroscopic imaging; and a non-transitory computer readable storage medium that stores a program that causes a computer to control the radiation irradiating device such that radiation is pulse-irradiated at the radiographic imaging device with a proportion of a radiation irradiation time period being set within a range of 12.5% to 80% with respect to each frame time period for capturing respective frame images according to a frame rate of the fluoroscopic imaging, while the capture of radiographic images is carried out at the radiographic imaging device synchronously with the pulse irradiation.

A radiation control method according to the third aspect of the invention is a method for a radiographic imaging system having a radiographic imaging device that is configured to perform fluoroscopic imaging comprising continuous capture of radiographic images, and a radiation irradiating device that irradiates radiation in pulse form with respect to the radiographic imaging device at a time of fluoroscopic imaging, the method including: controlling the radiation irradiating device such that radiation is pulse-irradiated at the radiographic imaging device with a proportion of a radiation irradiation time period being set within a range of 12.5% to 80% with respect to each frame time period for capturing respective frame images according to a frame rate of the fluoroscopic imaging, while the capture of radiographic images is carried out at the radiographic imaging device synchronously with the pulse irradiation.

In accordance with the present invention, there is the effect that fluoroscopic images having smooth motion can be captured.

The above exemplary embodiments do not limit the inventions relating to the claims, and it is not necessarily the case that all of the combinations of features described in the exemplary embodiments are essential to the means of the present invention for solving the problems of the prior art. Inventions of various stages are included in the above exemplary embodiments, and various inventions can be extracted by appropriately combining plural constituent features that are disclosed. Even if some of the constituent features are removed from all of the constituent features that are illustrated in the exemplary embodiments, such structures from which some constituent features are removed can be extracted as inventions provided that the effects of the present invention are obtained thereby.

What is claimed is:

1. A radiographic imaging system comprising:
a radiographic imaging device that is configured to perform fluoroscopic imaging comprising continuous capture of radiographic images;
a radiation irradiating device that irradiates radiation in pulse form with respect to the radiographic imaging device at a time of fluoroscopic imaging; and
a controller that controls the radiation irradiating device such that radiation is pulse-irradiated at the radiographic imaging device with a proportion of a radiation irradiation time period being set within a range of 12.5% to 80% with respect to each frame time period for capturing respective frame images according to a frame rate of the fluoroscopic imaging, while the capture of radiographic images is performed at the radiographic imaging device synchronously with the pulse irradiation,
wherein the controller controls the radiation irradiating device to set the radiation irradiation time period with respect to each frame time period such that, in a case in which a frame rate of fluoroscopic imaging is less than or equal to a first frame rate threshold value, radiation is pulse-irradiated with the proportion of the radiation irradiation time period with respect to each frame time period being set at a first proportion, and, in a case in which the frame rate of fluoroscopic imaging is less than or equal to a second frame rate threshold value that is lower than the first frame rate threshold value, radiation is pulse-irradiated with the proportion of the radiation irradiation time period with respect to each frame time period being set at a second proportion that is different from the first proportion.

2. The radiographic imaging system of claim 1, wherein the controller controls the radiation irradiating device such that radiation is pulse-irradiated with the proportion of the radiation irradiation time period with respect to each frame time period being set within a range of 33% to 80%.

3. The radiographic imaging system of claim 1, wherein the controller controls the radiation irradiating device such that the radiation irradiation time period in each frame time period is extended, and the proportion of the radiation irradiation time period with respect to each frame time period falls within the range of 12.5% to 80%.

4. The radiographic imaging system of claim 1, wherein the controller controls the radiation irradiating device such that, in a case in which a frame rate of fluoroscopic imaging is less than or equal to a first frame rate threshold value, radiation is pulse-irradiated with the proportion of the radiation irradiation time period with respect to each frame time period being set within a range of 12.5% to 80%, and, in a case in which the frame rate of fluoroscopic imaging is less than or equal to a second frame rate threshold value that is lower than the first frame rate threshold value, radiation is pulse-irradiated with the proportion of the radiation irradiation time period with respect to each frame time period being set within a range of 33% to 80%.

5. The radiographic imaging system of claim 4, wherein:
the first frame rate threshold value is from 15 fps to 120 fps; and
the second frame rate threshold value is from 5 fps to less than the first frame rate threshold value.

6. The radiographic imaging system of claim 1, further comprising:
a movement detecting unit that detects movement of a region to be imaged,
wherein, in a case in which an amount of movement detected by the movement detecting unit is greater than or equal to a predetermined threshold value, the controller controls the radiation irradiating device such that the proportion of the radiation irradiation time period with respect to each frame time period falls within the range of 12.5% to 80%.

7. The radiographic imaging system of claim 1, wherein, in a case in which a region to be imaged is a predetermined region, the controller controls the radiation irradiating device such that the proportion of the radiation irradiation time period with respect to each frame time period falls within the range of 12.5% to 80%.

8. The radiographic imaging system of claim 7, further comprising:
a storage unit,
wherein, the predetermined region is a region that is pre-designated as a region at which the movement of the region to be imaged is rapid, and whose region data is stored in advance in the storage unit.

9. The radiographic imaging system of claim 1, wherein:
the radiographic imaging device is configured to perform still imaging during fluoroscopic imaging; and
in a case in which still imaging is carried out during fluoroscopic imaging, the controller controls the radiation irradiating device such that the proportion of the radiation irradiation time period with respect to each frame time period in fluoroscopic imaging after the still imaging falls within the range of 12.5% to 80%.

10. The radiographic imaging system of claim 1, wherein the radiographic imaging device comprises an irradiation detecting unit that detects irradiation of radiation, and, when irradiation of radiation is detected by the irradiation detecting unit, the controller controls the radiographic imaging device so as to carry out capture of radiographic images after a resetting operation that removes charge accumulated due to dark current.

11. The radiographic imaging system of claim 1, wherein the controller and the radiographic imaging device are connectable by a cable, and if the controller and the radiographic imaging device are connected by the cable, wired communication is carried out therebetween, and if the controller and the radiographic imaging device are not connected by the cable, wireless communication is carried out therebetween.

12. A radiographic imaging system comprising:
a radiographic imaging device that is configured to perform fluoroscopic imaging comprising continuous capture of radiographic images;
a radiation irradiating device that irradiates radiation in pulse form with respect to the radiographic imaging device at a time of fluoroscopic imaging; and
a non-transitory computer readable storage medium that stores a program that causes a computer to control the radiation irradiating device such that radiation is pulse-irradiated at the radiographic imaging device with a proportion of a radiation irradiation time period being set within a range of 12.5% to 80% with respect to each frame time period for capturing respective frame images according to a frame rate of the fluoroscopic imaging, while the capture of radiographic images is carried out at the radiographic imaging device synchronously with the pulse irradiation,
wherein the program causes the computer to control the radiation irradiating device to set the radiation irradiation time period with respect to each frame time period such that, in a case in which a frame rate of fluoroscopic imaging is less than or equal to a first frame rate threshold value, radiation is pulse-irradiated with the proportion of the radiation irradiation time period with respect to each frame time period being set at a first proportion, and, in a case in which the frame rate of fluoroscopic imaging is less than or equal to a second frame rate threshold value that is lower than the first frame rate threshold value, radiation is pulse-irradiated with the proportion of the radiation irradiation time period with respect to each frame time period being set at a second proportion that is different from the first proportion.

13. A radiation control method for a radiographic imaging system having a radiographic imaging device that is configured to perform fluoroscopic imaging comprising continuous capture of radiographic images, and a radiation irradiating device that irradiates radiation in pulse form with respect to the radiographic imaging device at a time of fluoroscopic imaging, the method comprising:

controlling the radiation irradiating device such that radiation is pulse-irradiated at the radiographic imaging device with a proportion of a radiation irradiation time period being set within a range of 12.5% to 80% with respect to each frame time period for capturing respective frame images according to a frame rate of the fluoroscopic imaging, while the capture of radiographic images is carried out at the radiographic imaging device synchronously with the pulse irradiation, and controlling the radiation irradiating device to set the radiation irradiation time period with respect to each frame time period such that, in a case in which a frame rate of fluoroscopic imaging is less than or equal to a first frame rate threshold value, radiation is pulse-irradiated with the proportion of the radiation irradiation time period with respect to each frame time period being set at a first proportion, and, in a case in which the frame rate of fluoroscopic imaging is less than or equal to a second frame rate threshold value that is lower than the first frame rate threshold value, radiation is pulse-irradiated with the proportion of the radiation irradiation time period with respect to each frame time period being set at a second proportion that is different from the first proportion.

* * * * *